(12) United States Patent
Albert

(10) Patent No.: US 9,351,654 B2
(45) Date of Patent: May 31, 2016

(54) TWO ELECTRODE APPARATUS AND METHODS FOR TWELVE LEAD ECG

(71) Applicant: ALIVECOR, INC., San Francisco, CA (US)

(72) Inventor: David E. Albert, Oklahoma City, OK (US)

(73) Assignee: AliveCor, Inc., San Francisco, CA (US)

( * ) Notice: Subject to any disclaimer, the term of this patent is extended or adjusted under 35 U.S.C. 154(b) by 287 days.

(21) Appl. No.: 14/254,310

(22) Filed: Apr. 16, 2014

(65) Prior Publication Data

US 2014/0228665 A1  Aug. 14, 2014

Related U.S. Application Data

(63) Continuation-in-part of application No. 13/108,738, filed on May 16, 2011, now abandoned, which is a continuation-in-part of application No. 12/796,188, filed on Jun. 8, 2010, now Pat. No. 8,509,882.

(60) Provisional application No. 61/812,655, filed on Apr. 16, 2013.

(51) Int. Cl.
*A61B 5/00* (2006.01)
*A61B 5/0404* (2006.01)
*G06Q 50/22* (2012.01)
(Continued)

(52) U.S. Cl.
CPC ............. *A61B 5/0404* (2013.01); *A61B 5/0006* (2013.01); *A61B 5/0015* (2013.01); *A61B 5/0022* (2013.01); *A61B 5/044* (2013.01); *A61B 5/0408* (2013.01); *A61B 5/04028* (2013.01); *A61B 5/0432* (2013.01); *A61B 5/6898* (2013.01); *G06Q 50/22* (2013.01); *A61B 5/0205* (2013.01); *A61B 5/0452* (2013.01)

(58) Field of Classification Search
CPC ............................. A61B 5/0404; A61B 5/0006
USPC .......................................... 600/509, 323, 309
See application file for complete search history.

(56) References Cited

U.S. PATENT DOCUMENTS 3,717,857 A  2/1973  Evans
3,731,311 A  5/1973  Williams
(Continued)

FOREIGN PATENT DOCUMENTS

CH  675675  10/1990
CN  101828915 A  9/2010
(Continued)

OTHER PUBLICATIONS

U.S. Appl. No. 14/217,032, filed Mar. 17, 2014, Albert et al.
(Continued)

*Primary Examiner* — Nicole F Lavert
*Assistant Examiner* — Nadia A Mahmood
(74) *Attorney, Agent, or Firm* — Wilson Sonsini Goodrich & Rosati

(57) ABSTRACT

Described herein are methods, apparatuses, and systems for heart monitoring of a patient. The heart monitoring system can be used to take an electrocardiogram (ECG) using only two electrodes. A handheld device can be used to sequentially measure the electrical signal between different positions on a patient's body. The electrical signals can be processed and analyzed to prepare an ECG for the patient, including a 12-lead ECG.

36 Claims, 10 Drawing Sheets

(51) Int. Cl.
  *A61B 5/0402* (2006.01)
  *A61B 5/0408* (2006.01)
  *A61B 5/0432* (2006.01)
  *A61B 5/044* (2006.01)
  *A61B 5/0452* (2006.01)
  *A61B 5/0205* (2006.01)

(56) References Cited

U.S. PATENT DOCUMENTS

| | | |
|---|---|---|
| 3,768,014 A | 10/1973 | Smith et al. |
| 3,776,228 A | 12/1973 | Semler |
| 3,779,237 A | 12/1973 | Goeltz et al. |
| 3,779,249 A | 12/1973 | Semler |
| 3,782,367 A | 1/1974 | Hochberg et al. |
| 3,805,227 A | 4/1974 | Lester |
| 3,882,277 A | 5/1975 | DePedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |
| 4,045,767 A | 8/1977 | Nishihara et al. |
| 4,083,366 A | 4/1978 | Gombrich et al. |
| 4,095,050 A | 6/1978 | Beachem et al. |
| 4,221,223 A | 9/1980 | Linden |
| 4,230,127 A | 10/1980 | Larson |
| 4,231,031 A | 10/1980 | Crowther et al. |
| 4,250,888 A | 2/1981 | Grosskopf |
| 4,281,664 A | 8/1981 | Duggan |
| 4,295,472 A | 10/1981 | Adams |
| 4,312,358 A | 1/1982 | Barney |
| 4,318,130 A | 3/1982 | Heuer |
| 4,364,397 A | 12/1982 | Citron et al. |
| 4,367,752 A | 1/1983 | Jimenez et al. |
| 4,409,984 A | 10/1983 | Dick |
| 4,531,527 A | 7/1985 | Reinhold, Jr. et al. |
| 4,567,883 A | 2/1986 | Langer et al. |
| 4,572,182 A | 2/1986 | Royse |
| 4,580,250 A | 4/1986 | Kago et al. |
| 4,583,553 A | 4/1986 | Shah et al. |
| 4,622,979 A | 11/1986 | Katchis et al. |
| 4,625,730 A | 12/1986 | Fountain et al. |
| 4,803,625 A | 2/1989 | Fu et al. |
| 4,889,131 A | 12/1989 | Salem et al. |
| 4,920,489 A | 4/1990 | Hubelbank et al. |
| 4,938,228 A | 7/1990 | Righter et al. |
| 4,938,229 A | 7/1990 | Bergelson et al. |
| 4,958,641 A | 9/1990 | Digby et al. |
| 4,981,141 A | 1/1991 | Segalowitz |
| 5,012,814 A | 5/1991 | Mills et al. |
| 5,023,906 A | 6/1991 | Novas |
| 5,025,794 A | 6/1991 | Albert et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,136,555 A | 8/1992 | Gardos |
| 5,181,552 A | 1/1993 | Eiermann |
| 5,191,891 A | 3/1993 | Righter |
| 5,201,321 A | 4/1993 | Fulton |
| 5,218,969 A | 6/1993 | Bredesen et al. |
| 5,226,424 A | 7/1993 | Bible |
| 5,238,001 A | 8/1993 | Gallant et al. |
| D341,659 S | 11/1993 | Homayoun et al. |
| 5,259,387 A | 11/1993 | Depinto |
| 5,301,679 A | 4/1994 | Taylor |
| 5,304,186 A | 4/1994 | Semler et al. |
| 5,313,953 A | 5/1994 | Yomtov et al. |
| 5,321,618 A | 6/1994 | Gressman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,360,005 A | 11/1994 | Wilk |
| 5,365,935 A | 11/1994 | Righter et al. |
| 5,410,587 A | 4/1995 | Grunwell |
| 5,417,222 A | 5/1995 | Dempsey et al. |
| 5,433,736 A | 7/1995 | Nilsson |
| 5,452,356 A | 9/1995 | Albert |
| 5,466,246 A | 11/1995 | Silvian |
| 5,467,773 A | 11/1995 | Bergelson et al. |
| 5,481,255 A | 1/1996 | Albert et al. |
| 5,503,158 A | 4/1996 | Coppock et al. |
| 5,518,001 A | 5/1996 | Snell |
| 5,522,396 A | 6/1996 | Langer et al. |
| 5,539,705 A | 7/1996 | Akerman et al. |
| D372,785 S | 8/1996 | Sabri et al. |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Tanigushi et al. |
| 5,579,284 A | 11/1996 | May |
| D377,983 S | 2/1997 | Sabri et al. |
| 5,608,723 A | 3/1997 | Felsenstein |
| 5,634,468 A | 6/1997 | Platt et al. |
| 5,652,570 A | 7/1997 | Lepkofker |
| 5,661,699 A | 8/1997 | Sutton |
| 5,675,325 A | 10/1997 | Taniguchi et al. |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert et al. |
| 5,742,251 A | 4/1998 | Gerber |
| 5,748,103 A | 5/1998 | Flach et al. |
| 5,764,763 A | 6/1998 | Jensen et al. |
| 5,772,586 A | 6/1998 | Heinonen et al. |
| 5,818,788 A | 10/1998 | Kimura et al. |
| 5,825,718 A | 10/1998 | Ueki et al. |
| 5,827,179 A | 10/1998 | Lichter et al. |
| 5,840,020 A | 11/1998 | Heinonen et al. |
| 5,844,997 A | 12/1998 | Murphy, Jr. |
| 5,861,018 A | 1/1999 | Feierbach |
| 5,873,369 A | 2/1999 | Laniado et al. |
| 5,876,351 A | 3/1999 | Rohde |
| 5,877,675 A | 3/1999 | Rebstock et al. |
| 5,889,730 A | 3/1999 | May |
| 5,929,761 A | 7/1999 | Van Der Laan et al. |
| D414,870 S | 10/1999 | Saltzstein et al. |
| 5,970,388 A | 10/1999 | Will |
| 5,976,083 A | 11/1999 | Richardson et al. |
| 5,982,297 A | 11/1999 | Welle |
| 5,983,127 A | 11/1999 | Depinto |
| 6,008,703 A | 12/1999 | Perrott et al. |
| 6,024,705 A | 2/2000 | Schlager et al. |
| 6,037,704 A | 3/2000 | Welle |
| 6,048,319 A | 4/2000 | Hudgins et al. |
| D427,315 S | 6/2000 | Saltzstein et al. |
| 6,072,396 A | 6/2000 | Gaukel |
| 6,083,248 A | 7/2000 | Thompson |
| 6,084,510 A | 7/2000 | Lemelson et al. |
| 6,102,856 A | 8/2000 | Groff et al. |
| 6,153,532 A | 11/2000 | Dow et al. |
| 6,159,147 A | 12/2000 | Lichter et al. |
| 6,198,394 B1 | 3/2001 | Jacobsen et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk et al. |
| 6,343,049 B1 | 1/2002 | Toda |
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |

(56) References Cited

U.S. PATENT DOCUMENTS

| | | |
|---|---|---|
| 6,478,736 B1 | 11/2002 | Mault |
| 6,485,416 B1 | 11/2002 | Platt et al. |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,685,633 B2 | 2/2004 | Albert et al. |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,153,262 B2 | 12/2006 | Stivoric et al. |
| 7,162,294 B2 | 1/2007 | Rowlandson et al. |
| 7,188,151 B2 | 3/2007 | Kumar et al. |
| 7,222,054 B2 | 5/2007 | Geva |
| 7,236,818 B2 | 6/2007 | Mcleod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| 7,349,574 B1 | 3/2008 | Sodini et al. |
| 7,351,207 B2 | 4/2008 | Priemer |
| 7,354,400 B2 | 4/2008 | Asafusa et al. |
| 7,383,297 B1 | 6/2008 | Atsmon et al. |
| 7,415,304 B2 | 8/2008 | Rowlandson et al. |
| 7,444,116 B2 | 10/2008 | Ivanov et al. |
| 7,509,159 B2 | 3/2009 | Xue et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,596,405 B2 | 9/2009 | Kurzweil et al. |
| 7,603,148 B2 | 10/2009 | Michalak |
| 7,654,148 B2 | 2/2010 | Tomlinson, Jr. et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissila |
| 7,819,814 B2 | 10/2010 | Gavriely et al. |
| 7,846,104 B2 | 12/2010 | Macquarrie et al. |
| 7,904,160 B2 | 3/2011 | Brodnick et al. |
| 7,945,064 B2 | 5/2011 | O'Brien, Jr. et al. |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,078,136 B2 | 12/2011 | Atsmon et al. |
| 8,078,278 B2 | 12/2011 | Penner |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von Arx et al. |
| 8,224,429 B2 | 7/2012 | Prstojevich et al. |
| 8,265,907 B2 | 9/2012 | Nanikashvili et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 | 10/2012 | Baumann et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,543,185 B2 | 9/2013 | Yuen et al. |
| 8,548,770 B2 | 10/2013 | Yuen et al. |
| 8,700,137 B2 | 4/2014 | Albert et al. |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0111556 A1 | 8/2002 | Wegner |
| 2002/0143576 A1 | 10/2002 | Nolvak et al. |
| 2003/0004425 A1 | 1/2003 | Narimatsu et al. |
| 2003/0093002 A1 | 5/2003 | Kuo |
| 2003/0107487 A1 | 6/2003 | Korman et al. |
| 2003/0117987 A1 | 6/2003 | Brebner |
| 2003/0149344 A1 | 8/2003 | Nizan |
| 2003/0193839 A1 | 10/2003 | Singh |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0117212 A1 | 6/2004 | Kong et al. |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0228217 A1 | 11/2004 | Szeto |
| 2004/0236819 A1 | 11/2004 | Anati et al. |
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0193270 A1 | 8/2006 | Gehasie et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0063850 A1 | 3/2007 | Devaul et al. |
| 2007/0106179 A1 | 5/2007 | Bagha et al. |
| 2007/0156060 A1 | 7/2007 | Cervantes |
| 2007/0254604 A1 | 11/2007 | Kim |
| 2007/0265038 A1 | 11/2007 | Kim |
| 2008/0009759 A1 | 1/2008 | Chetham |
| 2008/0058670 A1 | 3/2008 | Mainini |
| 2008/0112885 A1 | 5/2008 | Okunev et al. |
| 2008/0146890 A1 | 6/2008 | LeBoeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |
| 2008/0228045 A1 | 9/2008 | Gao et al. |

(56) References Cited

U.S. PATENT DOCUMENTS

| | | |
|---|---|---|
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0184479 A1 | 7/2010 | Griffin, Jr. |
| 2010/0204758 A1 | 8/2010 | Boon et al. |
| 2010/0208434 A1 | 8/2010 | Kim et al. |
| 2010/0217099 A1 | 8/2010 | LeBoeuf et al. |
| 2010/0217100 A1 | 8/2010 | LeBoeuf et al. |
| 2010/0217345 A1 | 8/2010 | Wolfe et al. |
| 2010/0234746 A1 | 9/2010 | Sebelius |
| 2010/0256509 A1 | 10/2010 | Kuo et al. |
| 2010/0281261 A1 | 11/2010 | Razzell |
| 2010/0298171 A1 | 11/2010 | Pedersen et al. |
| 2010/0324378 A1 | 12/2010 | Tran et al. |
| 2010/0331631 A1 | 12/2010 | Maclaughlin |
| 2011/0015496 A1 | 1/2011 | Sherman et al. |
| 2011/0035927 A1 | 2/2011 | Griffin et al. |
| 2011/0060251 A1 | 3/2011 | Verma et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0160601 A1 | 6/2011 | Wang et al. |
| 2011/0182445 A1 | 7/2011 | Atsmon et al. |
| 2011/0235466 A1 | 9/2011 | Booij et al. |
| 2011/0275950 A1 | 11/2011 | Xue et al. |
| 2011/0288425 A1 | 11/2011 | Stewart |
| 2011/0301435 A1 | 12/2011 | Albert et al. |
| 2011/0301439 A1 | 12/2011 | Albert et al. |
| 2012/0051187 A1 | 3/2012 | Paulson |
| 2012/0053424 A1 | 3/2012 | Kenalty et al. |
| 2012/0071734 A1 | 3/2012 | Shimuta et al. |
| 2012/0123891 A1 | 5/2012 | Patel |
| 2012/0127833 A1 | 5/2012 | Ghen et al. |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0158090 A1 | 6/2012 | Chavan et al. |
| 2012/0171963 A1 | 7/2012 | Tsfaty |
| 2012/0172689 A1 | 7/2012 | Albert et al. |
| 2012/0179056 A1 | 7/2012 | Moulder et al. |
| 2012/0316413 A1 | 12/2012 | Liu et al. |
| 2013/0030259 A1 | 1/2013 | Thomsen et al. |
| 2013/0085364 A1 | 4/2013 | Lu et al. |
| 2013/0122810 A1 | 5/2013 | Kaufman |
| 2013/0156194 A1 | 6/2013 | Tanioka |
| 2013/0159699 A1 | 6/2013 | Torkkel |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0331663 A1 | 12/2013 | Albert et al. |
| 2014/0050321 A1 | 2/2014 | Albert et al. |
| 2014/0066798 A1 | 3/2014 | Albert et al. |
| 2014/0128758 A1 | 5/2014 | Galloway et al. |
| 2014/0194760 A1 | 7/2014 | Albert et al. |
| 2014/0221859 A1 | 8/2014 | Albert et al. |

FOREIGN PATENT DOCUMENTS

| | | |
|---|---|---|
| CN | 201918016 U | 8/2011 |
| CN | 102347804 A | 2/2012 |
| DE | 2506936 A | 9/1976 |
| DE | 4212670 A1 | 1/1994 |
| EP | 0631226 A1 | 12/1994 |
| EP | 1782229 A | 5/2007 |
| EP | 1181888 B1 | 9/2007 |
| EP | 1238633 B1 | 10/2008 |
| EP | 2030565 A1 | 3/2009 |
| EP | 2116183 B1 | 2/2012 |
| FR | 2740426 A1 | 4/1997 |
| GB | 2181554 | 4/1987 |
| GB | 2408105 A | 5/2005 |
| JP | 59-122032 A | 7/1984 |
| JP | 59-190742 A | 10/1984 |
| JP | 63-072231 A | 4/1988 |
| JP | 63-294044 A | 10/1988 |
| JP | 1-244328 A | 9/1989 |
| JP | 5-167540 A | 7/1993 |
| JP | 6-326669 A | 11/1994 |
| JP | 2002191562 A | 7/2002 |
| JP | 2002-261731 A | 9/2002 |
| JP | 2003-010177 A | 1/2003 |
| JP | 2005-295378 A | 10/2005 |
| JP | 2012-065073 A | 3/2012 |
| KR | 10-2010-0059198 A | 6/2010 |
| MX | 2009011781 A1 | 5/2011 |
| WO | WO 82/00910 A1 | 3/1982 |
| WO | WO 88/05282 A1 | 7/1988 |
| WO | WO 90/08361 A1 | 7/1990 |
| WO | WO 92/06551 A1 | 4/1992 |
| WO | WO 97/31437 A1 | 8/1997 |
| WO | WO 98/38611 A1 | 9/1998 |
| WO | WO 99/44494 A1 | 9/1999 |
| WO | WO 00/41620 A1 | 7/2000 |
| WO | WO 01/47597 A2 | 7/2001 |
| WO | WO 01/57619 A2 | 8/2001 |
| WO | WO 02/080762 A1 | 10/2002 |
| WO | WO 03/075118 A2 | 9/2003 |
| WO | WO 03/094720 A1 | 11/2003 |
| WO | WO 2004/037080 A1 | 5/2004 |
| WO | WO 2006/001005 A2 | 1/2006 |
| WO | WO 2007/014545 A2 | 2/2007 |
| WO | WO 2007/088315 A1 | 8/2007 |
| WO | WO 2008/005015 A1 | 1/2008 |
| WO | WO 2008/066682 A2 | 6/2008 |
| WO | WO 2010/025166 A1 | 3/2010 |
| WO | WO 2010/108287 A1 | 9/2010 |
| WO | WO 2010/113354 A1 | 10/2010 |
| WO | WO 2010/144626 A1 | 12/2010 |
| WO | WO 2011/006356 A1 | 1/2011 |
| WO | WO 2011/008838 A1 | 1/2011 |
| WO | WO 2011/014292 A1 | 2/2011 |
| WO | WO 2011/022942 A1 | 3/2011 |
| WO | WO 2011/040877 A1 | 4/2011 |
| WO | WO 2011/040878 A1 | 4/2011 |
| WO | WO 2011/113070 A1 | 9/2011 |
| WO | WO 2011/137375 A2 | 11/2011 |
| WO | WO 2011/156374 A2 | 12/2011 |
| WO | WO 2012/046158 A1 | 4/2012 |
| WO | WO 2012/108895 A1 | 8/2012 |
| WO | WO 2012/129413 A1 | 9/2012 |
| WO | WO 2012/160550 A1 | 11/2012 |
| WO | WO 2013/036307 A1 | 3/2013 |
| WO | WO 2013/066642 A1 | 5/2013 |
| WO | WO 2013/093690 A1 | 6/2013 |
| WO | WO 2013/122788 A1 | 8/2013 |
| WO | WO 2013/138500 A1 | 9/2013 |
| WO | WO 2013/155196 A2 | 10/2013 |
| WO | WO 2013/192166 A1 | 12/2013 |

OTHER PUBLICATIONS

U.S. Appl. No. 14/328,962, filed Jul. 11, 2014, Thomson et al.

(56) References Cited

OTHER PUBLICATIONS

U.S. Appl. No. 14/494,191, filed Sep. 23, 2014, Albert et al.
U.S. Appl. No. 14/479,105, filed Sep. 5, 2014, Albert et al.
Adidas miCoach Pacer Review: Like Nike+, Only Better; printed from website http://gizmodo.com/5479456/adidas• printed on Mar. 4, 2010• 5 pages.
Australian Design Awards. Heartplus Micro; printed from website http://www.designawards.com/au; printed on Apr. 12, 2002 • 6 pages.
Bajaj, M.D.; "Event Recording in Ambulatory Patients with Syncopal Events"; University of Kansas; Wichita, Kansas; (no date); pp. 15-18; printed on or before Apr. 14, 2010.
Bluetooth. Headset Profile (HSP), printed from website http://bluetooth.com/English/Techmology/Works/Pates/HSP.asgx, printed on May 12, 2010.
Bramanti et al., Multichannel telemetric system for biomedical signals via switched telephone lines, Medical and Biological Engineering and Computing, Sep. 1982, vol. 20, No. 5, pp. 653-656.
Burke, "A Micropower Dry-Electrode ECG Preamplifier", IEEE Transactions on Biomedical Engineering, Feb. 2000, vol. 47, No. 2, pp. 155-162.
Card Guard CG-6108 ACT Ambulatory Cardiac Telemetry Brochure; Card Guard; The Telemedicine Company: Switzerland; 2006; 2 pages.
Cardiocomm Solutions; GEMS AIR. (PC based ECG management) printed from website http://www.cardiocommsolutions/com; printed on Mar. 19, 2010; 1 page.
Charuvastra. Transtelephonic Cardiac Event Recording for Arrhythmia Surveillance; printed from website http://tchin.org/resource room/c art• printed on Mar. 26, 2010• 2 pages.
Cheng, Allen C.; "Real-Time Cardiovascular Diseases Detection on a Smartphone"; Departments of Electrical and Computer Engineering, Bioengineering, Neurological Surgery and Computer Science; University of Pittsburgh; Pittsburgh, PA; printed on or before Apr. 14, 2010.
Creative. PC-80B Portable ECG Monitor w/sd card extension slot; printed from website www.amazon.com/Portable-Monitor-extension-leather-shipping/dp/B0010jWKUE; printed on Feb. 4, 2010• 5 pages.
Deveau, "Health Care eyes smart phones to heal ills", printed from the website http://www.theQiobeandmail.com on Sep. 17, 2009, 4 pages.
Dinh. Heart activity monitoring on smartphone. IPCBEE-Int conf Biomedical Eng and Technol. Jun. 17-19, 2011. 11:45-49.
Dobrev, et al., Bootstrapped two-electrode biosignal amplifier, Med Bioi Eng Comput, 2008, 7 pages.
Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).
Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http:1/hypertextbook.com/facts/2003/ChrisDAmbrose.shtml).
European search report and opinion dated Nov. 21, 2014 for EP Application No. 11865699.0.
Favorite Plus. Handheld Easy ECG Monitor—Handheld Easy EKG Monitor; printed from website www.favoriteplus.com/easy-ecg-handgeld-monitor-fp; printed on Feb. 4, 2010; 2 pages.
Favorite Plus. Handheld ECG Monitor—Handheld EKG Monitor at Favoriteplus.com; printed from website www.favoriteplus.com/handheld-ecg-ekg-monitor; printed on Feb. 4, 2010; 3 pages.
Favorite Plus. Handheld ECG Monitor—Handheld EKG Monitor InstantCheck; printed from website http://www.favoriteplus.com/instanchcheck-hand held-ecg-ekg-monitor; printed on Feb. 4, 2010; 2 pages.
Ferrick, M.D.; "Holter Monitoring and cardiac Event Recording in Assessing Symptomatic Patients"; Albert Einstein College of Medicine; Bronx, New York; (no date)• pp. 11-14. printed on or before Apr. 14, 2010.

FREE2MOVE. Vitaphone 2300; www.free2move.us/News/NewsVitaghone240105.htm printed May 12, 2010.
Fulford-Jones, et al., "A Portable, Low-Power, Wireless Two-Lead EKG System", Division of Engineering and Applied Sciences, Harvard University, Sep. 2004, 4 pages.
Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.
GBI Portal. Qualcomm's wireless reach mHealth project to improve cardiovascular disease in resource scarce China; Feb. 17, 2012; 7 pgs. Retrieved Mar. 19, 2014 from www.intergrallc.com/2012/02/17/qualcooms-wireless-reach-mhealth-project-to-improve-cardiovascular-disease-in-resource-scarce-china/.
Gillette, M.D.; "Diagnosis of Pediatric Arrhythmias with Event Recording"; Medical University of South Carolina; Charleston, South Carolina; (no date); pp. 25-32; printed on or before Apr. 14, 2010.
Grier, James W.; "How to use 1-lead ECG recorders to obtain 12-lead resting ECGs and exercise ("stress") ECGs"; Department of Biological Sciences: printed from website http://www.ndsu.edu/pubweb/rvgrier; printed on Jun. 7, 21010; 13 pages.
Hannaford, Kat; "How to Turn Your iPhone Into a Laser, Fan or Flashlight"; printed from website htto://m.qizmodo.com/5534904• printed on Feb. 3, 2011.
Hartmann, "ECG Front-End Design is Simplified with MicroConverter" AnalogDialogue, Nov. 2003, vol. 37, pp. 1-5.
Hayes, M.D.; "Approaches to Diagnosing Transient Arhythmias" An Overview; Mayo Clinic; Rochester Minnesota; (no date); pp. 7-10; printed on or before Apr. 14, 2010.
Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.orglhlasurvival 1.html).
Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/0ctober2007/CiincalHuang0ctober2007.aspx).
IMEC News; IMEC extends flexible ECG patch to enable arrhythmia detection; printed from website http://www2.imec.be/imeC' printed on Aug. 18, 2009 1 page.
Instromedix. Cardiac Event Recording Faq's; Instromedix A Card Guard Company, San Diego, CA.; printed from website www.instromedix.com/pdf/products/cardiac; printed on or before Apr. 14, 2010.
Instromedix. The Arrhythmia Monitoring System; King of Hearts Express AF Recorder Brochure from Instromedix• A CardGuard Company; Rosemont IL; 2004• 3 pages.
International search report and written opinion dated Feb. 17, 2012 for PCT/US2011/039445.
International search report and written opinion dated Apr. 27, 2012 for PCT/US2011/053708.
International search report and written opinion dated May 15, 2013 for PCT/US2013/023370.
International search report dated Sep. 1, 2014 for PCT/US2014/034350.
International search report dated Dec. 10, 2013 for PCT/US2013/057576.
International search report dated Dec. 17, 2013 for PCT/US2013/055458.
Jenkins II, W.; Time/Frequency Relationships for an FFT-Based Acoustic Modem; Naval Postgraduate School; pp. 1-1 02; Sep. 2010 (http://edocs.nps.edu/npspubs/scholarly/theses/201 0/Sep/1 OSep_Jenkins.pdf) printed Oct. 2, 2013.
Kim, et al., "Detection of Atrial Fibrillation Episodes using Multiple Heart Rate Variabili!Y_Features in Different Time Periods", 2008, 4 pages.
Koerner. The Author's Metrics; Wired Magazine Article; New York, NY; Jul. 2009; p. 93-126.
Kumar, M.D., "Zio Patch", printed from website http://www.irhythmtech.com/zio-solution/zio-gach/, grinted on Apr. 12, 2010.

(56) References Cited

OTHER PUBLICATIONS

Kumparak, Greg; "Visa officially announces their case that turns your iPhone into a credit card (and we've got pies!)"; May 17, 2010; printed from website www.mobilecrunch.com• printed on Feb. 3, 2011.
Lau et al. Validation of an iPhone ECG application suitable for community screening for silent atrial fibrillation—a novel way to prevent stroke (Presentation Abstract 16810); American Heart Association 2012 Scientific Sessions and Resuscitation Science Symposium; 126(1); Nov. 20, 2012.
Lau, et al. iPhone ECG application for community screening to detect silent atrial fibrillation: A novel technology to prevent stroke. Int J Cardiol. Apr. 30, 2013;165(1):193-4.
Lau, et al. Performance of an Automated iPhone ECG Algorithm to Diagnose Atrial Fibrillation in a Community AF Screening Program (SEARCH-AF). Heart, Lung and Circulation. 2013; 22(1): S205; 2013 (Abstracts for the Cardiac Society of Australia and New Zealand Annual Scientific Meeting and the International Society for Heart Research Australasian Section Ann. Scientific Meeting, Aug. 8-11, 2013, Gold Coast).
Leijdekkers et al., "Trial Results of a Novel Cardiac Rhythm Management System using Smart Phones and wireless ECG Sensors", Proceedings of the th International Conf. on Smart homes and health Telematics., Jul. 1-3, 2009, Tours, France.
Levkov et al., "Removal of power-line interference from the ECG: a review of the subtraction procedure" BioMedical Engineering Online 2005, printed from website httg://www.biomedical-engineeringonline.com/contenU4/1/50 pp. 1-18.
Lowres, et al. Screening Education and Recognition in Community pHarmacies of Atrial Fibrillation to prevent stroke in an ambulant population aged >=65 years (SEARCH-AF stroke prevention study): a cross-sectional study protocol. BMJ Open. Jun. 25, 2012; 2(3); pii: e001355. doi: 10.1136/bmjopen-2012-001355.
M Med Choice printed from website http://www.choicemmed.con/1xwm .asp; printed on Dec. 28, 2009• 1 page.
M Med Choice. Handheld ECG Monitor MD100A1; printed from website http://www.choicemmed.com/productshow.as_p; printed on Dec. 28, 2009; 2 pages.
M Med Choice. Handheld ECG Monitor MD100B; printed from website http://www.choicemmed.com/productshow.asp; printed on Dec. 28, 2009• 2 pages.
M Med Choice. Handheld ECG Monitor Brochure; M Med Choice, Beijing Choice Electronic Technology Co. LTD. • published on or before Apr. 14, 2010.
MacFarlane, et al. Resting 12-lead ECG electrode placement and associated problems; SCST update 1995; 15pgs. Printed Feb. 18, 2014 from www.scst.org.uk/resources/RESTING_12.pdf.
Mauvila ECG Tutorial; Basic ECG Interpretation Tutorial; Sections 1-12; printed from website http://mauvila.com/ECG/ecg.htm• printed on Mar. 26, 2010• 56 pages.
Medgadget. Zio Patch Wins Medical Design Award MedGadget interne journal of emerging medical technologies, printed from website http://medaadaet.com/archives/2010/04/zio_patch_wins_medial_design_award_1.html.
MiCardioMobile: Remote Wireless Cardiac Rehabilitation Monitoring printed from website htto://alivetec.cable.nu/cardiomobile• printed on or before Apr. 14, 2010.
Mobility Mind. Use your Treo 650 as a portable ECG monitoring device, Mobility Mind Celebrating mobile Internet lifestyle and culture, Sep. 14, 2005, printed from website httg://www.treotoday.net/2005/09/14/use-your-treo-650-as-a-portable-ecg-monitoring-device/.
Modem Protocols Explained; ftp://kermit.columbia.edu/kermit/cu/protocol.html; 5 pgs.; printed Oct. 2, 2013.
Modem Tutorial; http://www.lsu.edu/OCS/its/unix/tutoriai/ModemTutoriai/ModemTutorial.html; 2 pgs.; printed Oct. 2, 2013.
Muench, Frederick, PhD; "HRV: The Manurfacturers and Vendors Speak; The portable StressEraser Heart Rate Variability Biofeedback Device: Background and Research" • Biofeedback vol. 36 Issue 1, pp. 35-39• published Spring 2008.

Murph. RedEye mini converts iPhone, iPad or iPod touch into IR-beaming universal remote; printed from website http://www.engadget.com/2010/03/02/redeye; printed on Mar. 2, 2010; 3 pages.
Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).
Neuroreille; Audiometry; web version as of Oct. 14, 2008; 1 pg.; printed Jun. 6, 2012 (http://www.neuroreille.com/promenade/english/audiometry/audiometry.htm).
New Professional Quality ECGEKG Portable Heart Monitor; printed from website http://cgibay.com/ws/eBayiSAPI.dll• printed on Feb. 4, 2010• 3 pages.
Notice of allowance dated Jan. 8, 2014 for U.S. Appl. No. 14/015,303.
Notice of allowance dated Jan. 27, 2014 for U.S. Appl. No. 14/015,303.
Notice of allowance dated Feb. 26, 2014 for U.S. Appl. No. 14/015,303.
Notice of allowance dated May 23, 2014 for U.S. Appl. No. 13/108,738.
Notice of allowance dated Jul. 9, 2013 for U.S. Appl. No. 12/796,188.
Notice of allowance dated Aug. 28, 2012 for U.S. Appl. No. 13/420,520.
Notice of allowance dated Dec. 4, 2013 for U.S. Appl. No. 14/015,303.
Office action dated Jan. 2, 2014 for U.S. Appl. No. 13/108,738.
Office action dated Jun. 18, 2012 for U.S. Appl. No. 13/420,520.
Office action dated Sep. 12, 2014 for U.S. Appl. No. 13/108,738.
Office action dated Oct. 6, 2014 for U.S. Appl. No. 14/252,044.
Office action dated Oct. 29, 2012 for U.S. Appl. No. 12/796,188.
Office action dated Nov. 19, 2014 for U.S. Appl. No. 13/969,446.
Omron Portable ECG EKG Handheld HCG-801 Monitor; printed from website http://www.amazon.com/Omron-Portable-Handheld-HCG-801-Monitor/dp/B0019WH3EO• printed on Feb. 24, 2010• 5 pages.
Omron Portable ECT Monitor; printed from website http://www.target.com/gp/detail.html; printed on Mar. 26, 2010• 1 page.
Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.
Perez, Sarah; No NFC? No Problem; New Startup Zoosh Provides Workaround Technology (Jun. 20, 2011 ); printed on or before Jun. 27, 2011 from website; 2 pgs.; (http://www.readwriteweb.com/archives).
Prystowsky, M.D., "The Clinical Application, Diagnostic Yield and Cost Considerations of Cardiac Event Recorders", Indianapolis, Indiana (no date) pp. 19-23. printed on or before Apr. 14, 2010.
Prystowsky, M.D.; "Chairmans Introduction"; Duke University Medical Center; Indianapolis, Indiana• (no date)• pp. 5-6• printed on or before Apr. 14, 2010.
Prystowsky, M.D.; "Chairmans Summary"; Duke University Medical Center; Indianapolis Indiana; (no date); pp. 39-40• printed on or before Apr. 14, 2010.
Puurtinen, et al., Best Electrode Locations for a Small Bipolar ECG Device: Signal Strength Analysis of Clinical Data, Annals of Biomedical Engineering, vol. 37, No.s 2, Feb. 2009 (© 2008) pp. 331-336.
Raju Heart-Rate and EKG Monitor Using the MSP430FG439, SLAA280—Oct. 2005—Revised Sep. 2007, 11 pages.
Readmyheart Personal Handheld ECG Monitor with Free Illustrator Book & Free Electrodes V2.2; printed from website http://www.amazon.com/Readmyheart-Personai-Handheld-illustrator-Eiectrodes/dp/B0010AN63W; printed on Mar. 26, 2010; 4 pages.
Read-My-Heart. ECG Machine Handheld Read MyHeart; (product item No. HH-3413) printed from website http://www.helioliving.com/ECG-Machi ne-Handheld-ReadMyHea rt; printed on Feb. 4, 2010; 1 page.

(56) References Cited

OTHER PUBLICATIONS

Ricker. Square payment dongle demoed for iPhone toting hippies and you (video); printed from website http://www.engadget.com/2010/01/18/square-payment; printed on Jan. 18, 2010; 6 pages.

Rockwood. The Networked Body Magazine Article from Fast Talk Magazine; Jul./Aug. 2009; pp. 19-26.

Salahuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.

Saxon, et al. iPhone rhythm strip—the implications of wireless and ubiquitous heart rate monitoring. JACC; 59(13): E726; Mar. 2012.

Saxon. Ubiquitous Wireless ECG Recording: A Powerful Tool Physicians Should Embrace. J Cardiovasc Electrophysiol. 24(4): pp. 480-483; Apr. 2013.

Semler, M.D.; "The Future of Cardiac Event Monitoring"; St. Vincent Hospital and Medical Center; Portland Oregon; (no date); pp. 33-37; printed on or before Apr. 14, 2010.

SFO Medical. Choice Portable Handheld ECG EKG Monitor; printed from website http://www.amazon.com/Choice-Portable-Handheld-ECG-Monitor/dp/B001Q74VOM; printed on Mar. 26, 2010; 1 page.

Shenzhen New Element Med. Equipment. Wireless ECG Monitoring System, printed from website http://www.alibaba.com/product-gs/248168581/Wireless_ECG_Monitoring_system.html., printed on Mar. 26, 2010.

Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.

Smith. Smartphone may keep the cardiologist away, The Independent, Health & Families, Mar. 5, 2010, printed from website http://www.independent.co.uk/life-style/health-and-families/healthnews/smartghone-may-keep-the-cardiologist-away-1916652.html, printed on Mar. 26, 2010.

Stevens, "Apple's Seamlessly Embedded Heart Rate Monitor could turn the iPhone into a new-age mood ring", printed from the website http://www.enaadaet.com on May 6, 2010, 3 pages.

Taleb Medical. Observer Hand-held ECG Monitor MD100B; (no date); printed on or before Apr. 14, 2010.

Tei, et al., New index of combined systolic and diastolic myocardial performance: a simple and reproducible measure of cardiac function—a study in normals and dilated cardiomyopathy; J Cardiol.; 26(6):357-366; Dec. 1995.

Texas Instruments. Information for Medical Applications, "Biophysical Monitoring-Electrocardiogram (ECG) Front End", Apr. 2004, 2 pages.

Tschida. Power A's New Case Turns Your iPhone Into a Universal Remote; printed from website http://appadvice.com/appnn; printed on Mar. 1, 2010• 2 pages.

Vanhemert, Kyle; "XWave Headset Lets You Control iPhone Apps With Your Brain"; Sep. 8, 2010; printed from website http://gizmodo.com; printed on Sep. 8, 2010.

Vitaphone. Telemedicine since 1999: Modern health management is our special subject. 3 pgs. Retrieved Mar. 19, 2014 from www.vitaphone.de/en/company/history-of-vitaphone/.

Wikimedia Laboratories; Acoustics; web archive version dated Jan. 25, 2009; 2 pgs.; printed Jun. 6, 2012 (http://liveweb.archive.org/http://en.labs.wikimedia.org/wild/Acoustics).

Wikipedia ."Pulse oximetry", printed from website httg://en.wikigedia.orq on May 10, 2010, 4 pages.

Wikipedia; Aliasing; web version as of Apr. 3, 2011; S pgs.; printed Jun. 6, 2012 (http://liveweb.archive.org/http://en.wikipedia.org/w/index.php?title=Aiiasing&oldid=422141882).

Wikipedia; Hearing Range; web version as of Feb. 6, 2010; S pgs.; printed Jun. 6, 2012 (http://web.archive.org/web/201 00206213741/http://en.wikipedia.org/wiki/Hearing_range).

Wisneski, C.; Ultrasonic Local Area Communication; http://alumni.media.mit.edu/-wiz/ultracom.html; 2 pgs.; printed Oct. 2, 2013.

Woodward et al; "Bio-Potentiai-To-Frequency Converter/Modulator"; Electronic Design• Aug. 1999• p. 117.

Ziegler, Chris; "EPI Life phone sports ECG function, can let doctors know if you're gonna make it"; printed from website www.enoadoet.com/2010/06/; Jun. 17 2010.

International search report and written opinion dated Sep. 1, 2014 for PCT/US2014/034350.

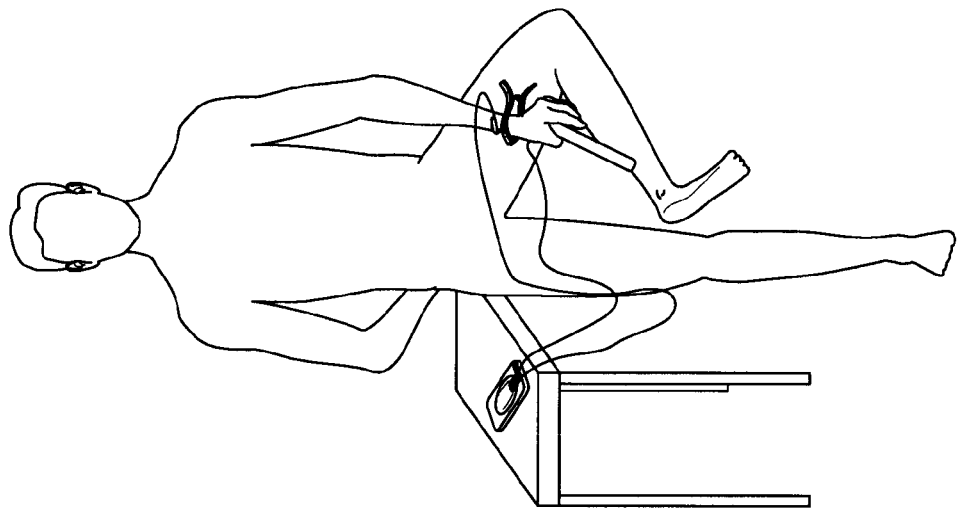
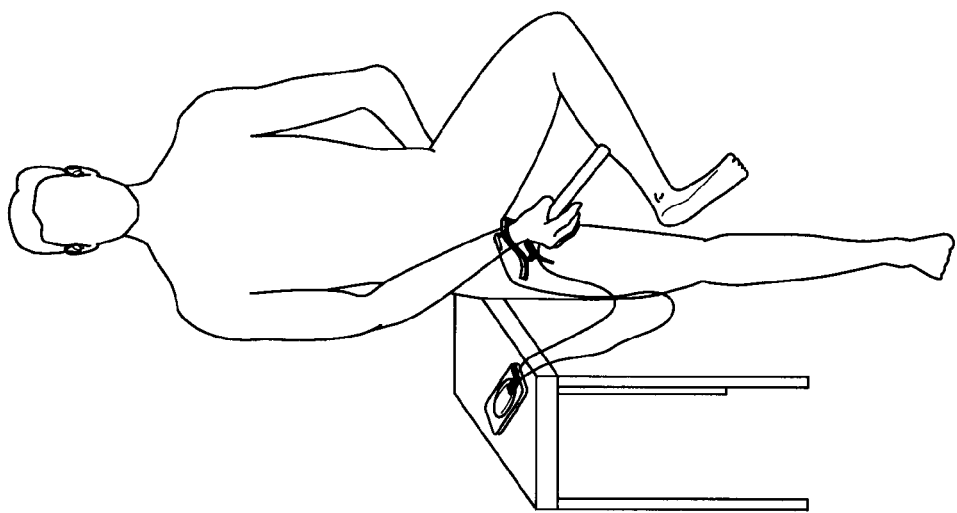
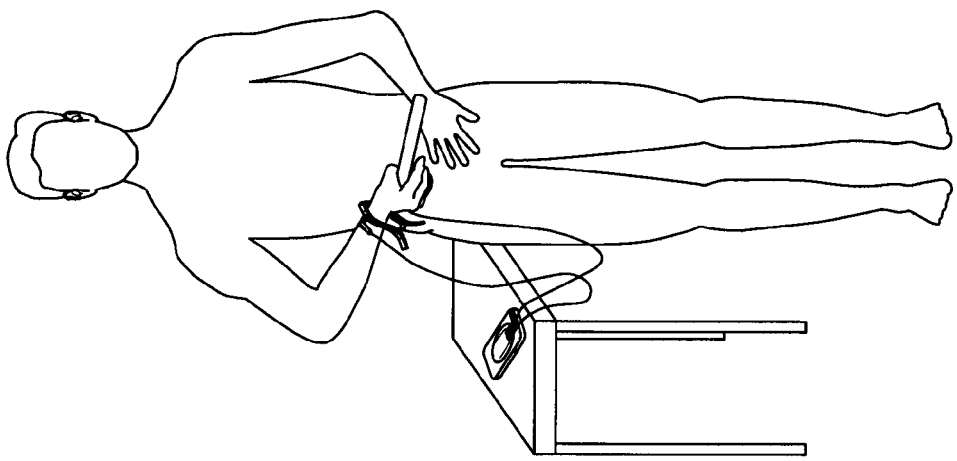
FIG. 7C
FIG. 7B
FIG. 7A

TWO ELECTRODE APPARATUS AND METHODS FOR TWELVE LEAD ECG

CROSS REFERENCE TO RELATED APPLICATIONS/INCORPORATION BY REFERENCE STATEMENT

This application is a continuation-in-part of U.S. Ser. No. 13/108,738, filed May 16, 2011, which is a continuation-in-part of U.S. Ser. No. 12/796,188, filed Jun. 8, 2010, now U.S. Pat. No. 8,509,882, each of which is hereby expressly incorporated herein by reference in its entirety. This application also claims priority to U.S. Provisional Application No. 61/812,655 filed on Apr. 16, 2013 which is hereby expressly incorporated herein by reference in its entirety.

BACKGROUND OF THE INVENTIVE CONCEPTS

1. Field of the Inventive Concepts

The presently claimed and disclosed inventive concept(s) relates generally to heart monitoring devices and methods and, more particularly, but not by way of limitation, to devices, systems and software for generating and providing one or more 12-lead electrocardiograms utilizing only two electrodes.

2. Brief Description of Related Art

Electrocardiography has been used to study the electrical activity of the heart. Electrocardiograms (ECG) can be recorded or taken using electrodes placed on the skin of a patient. The electrical signals recorded between any two electrodes placed on the skin of the patient are referred to as "leads." Varying numbers of electrodes and leads can be used to take the ECG. Exemplary numbers of leads used conventionally for taking ECGs are 3, 5, and 12 leads. For a standard 12-lead ECG, ten electrodes are used with six electrodes positioned on the chest and one electrode on each of the patient's arms and legs.

FIG. 1 is a pictorial representation of the 10 electrodes of a conventional electrocardiograph being placed on the patient for obtaining a standard 12-lead ECG. The electrode placed on the right arm is commonly referred to as RA. The electrode placed on the left arm is referred to as LA. The RA and LA electrodes are placed at the same location on the left and right arms, preferably but not necessarily near the wrist. The leg electrodes can be referred to as RL for the right leg and LL for the left leg. The RL and LL electrodes are placed on the same location for the left and right legs, preferably but not necessarily near the ankle.

FIG. 2 illustrates the placement of the six electrodes on the chest in the prior art arrangement with such electrodes being labeled $V_1$, $V_2$, $V_3$, $V_4$, $V_5$, and $V_6$. $V_1$ is placed in the fourth intercostal space, for example between ribs 4 and 5, just to the right of the sternum. $V_2$ is placed in the fourth intercostal space, for example between ribs 4 and 5, just to the left of the sternum. $V_3$ is placed in the fifth intercostal space midway between electrodes $V_2$ and $V_4$. $V_4$ is placed in the fifth intercostal space between ribs 5 and 6 on the left mid-clavicular line. $V_5$ is placed horizontally even with $V_4$ on the left anterior axillary line. $V_6$ is placed horizontally even with $V_4$ and $V_5$ on the left mid-axillary line.

The electrocardiograph then calculates and outputs three limb lead waveforms. Limb leads I, II, and III are bipolar leads having one positive and one negative pole. Lead I is the voltage between the left arm (LA) and right arm (RA), e.g. I=LA–RA. Lead II is the voltage between the left leg (LL) and right arm (RA), e.g. II=LL–RA. Lead III is the voltage between the left leg (LL) and left arm (LA), e.g. III=LL–LA. Leads I, II and III are commonly referred to as "limb leads."

Unipolar leads also have two poles; however, the negative pole is a composite pole made up of signals from multiple other electrodes. In a conventional cardiograph for obtaining a 12-lead ECG, all leads except the limb leads are unipolar (aVR, aVL, aVF, $V_1$, $V_2$, $V_3$, $V_4$, $V_5$, and $V_6$). Augmented limb leads (aVR, aVL, and aVF) view the heart from different angles (or vectors) and are determined from RA, RL, LL, and LA. For example, the augmented vector right (aVR) positions the positive electrode on the right arm, while the negative electrode is a combination of the left arm electrode and the left leg electrode, which "augments" the signal strength of the positive electrode on the right arm. Thus the augmented vector right (aVR) is equal to RA–(LA+LL)/2 or –(I+II)/2. The augmented vector left (aVL) is equal to LA–(RA+LL)/2 or (I–II)/2. The augmented vector foot (aVF) is equal to LL–(RA+LA)/2 or (II–I)/2.

The six electrodes on the chest of the patient are close enough to the heart that they do not require augmentation. A composite pole called Wilson's central terminal (often symbolized as $CT_W$, $V_W$, or WCT) is used as the negative terminal. Wilson's central terminal is produced by connecting the electrodes RA, LA, and LL together, via a simple resistive network, to give an average potential across the body, which approximates the potential at an infinite distance (i.e. zero). Wilson's central terminal, WCT, is calculated as (RA+LA+LL)/3.

FIG. 3 illustrates an example Lead I annotated to show PQRST waves generated by a 12-lead electrocardiograph. The identification and measurement of the PQRST waves based on the electrocardiogram is known in the art. FIG. 4 illustrates an example of a 12-lead electrocardiogram in a conventional format.

While a conventional 12-lead electrocardiogram gives very useful information concerning the health and condition of an individual's heart, the conventional electrocardiograph equipment is expensive and the procedure is not normally available in areas other than hospitals and medical doctors' offices. Therefore monitoring is not done frequently even in wealthy countries, and in poorer areas of the world an electrocardiograph may not even be available. To significantly reduce costs of obtaining an electrocardiogram, a 2-electrode electrocardiograph device as described in U.S. Pat. No. 8,301,232 was marketed. The 2-electrode electrocardiograph device utilizes a smart phone connected to and at least partially surrounded by a phone protective case incorporating and supporting the two electrodes. Such devices significantly simplify and reduce the cost of obtaining an electrocardiogram, although such an electrocardiogram does not include as much information as a 12-lead electrocardiogram produced by an electrocardiograph having 10 electrodes. The 12-lead electrocardiogram produced by the 10-electrode electrocardiograph offers additional and important heart-related information to the cardiologist, allowing the diagnosis of conditions like heart attacks (myocardial infarctions) that a single-lead ECG cannot do. It would be advantageous if a readily available and inexpensive device could generate and produce an electrocardiogram that substantially replicates the 12-lead electrocardiogram produced by a 10-electrode electrocardiograph.

SUMMARY OF THE DISCLOSURE

In general, described herein are apparatuses, methods and systems for producing an electrocardiogram that substantially replicates the electrocardiogram produced by a 10-electrode electrocardiograph but using an electrocardiograph device having only two electrodes. In one embodiment, the electrocardiograph device has a first electrode assembly with a first electrode adapted to measure an electrical signal on a patient's body, and a second electrode assembly with a second electrode adapted to measure an electrical signal at another location on the patient's body. The electrocardiograph device also includes control circuitry configured to measure electrocardiogram signals between the first and second electrodes, and a data transmission module configured to transmit the measured electrocardiogram signals to a portable computing device by a wired or wireless transmission system and protocol such as, for example, those known in the art as USB, WI-FI®, BLUETOOTH®, NFC, or as audible or ultrasonic sound signals.

The electrocardiograph device can be used in combination with a portable computing device to form an electrocardiograph. The portable computing device is provided with computer hardware including a processor in communication with a non-transitory computer readable medium. The non-transitory computer readable medium stores software that includes instructions that when executed by the processor causes the processor to record the electrocardiogram signals between the first electrode and the second electrode while the first and second electrodes are sequentially placed in predetermined paired positions on a patient's body that are known by the processor. In one embodiment the processor is caused to (a) calculate an average PQRST beat from the measured electrocardiogram signals as the first and second electrodes are sequentially placed in Limb Lead I, II, and III positions on a patient's body for a time required to measure at least one heartbeat in each Limb Lead position, the Limb Lead positions known by the processor; (b) use the relationship (Lead III=Lead II−Lead I) to time-align and display Limb Leads I, II, and III; and (c) calculate and display augmented Leads aVR, aVL, and aVF from the time-aligned Limb Leads I, II, and III.

The software can further include instructions that when executed by the processor causes the processor to calculate and display average time-aligned Leads V1, V2, and V3 from the measured electrocardiogram signals obtained from sequentially placing one of the first and second electrodes in a V1, V2, and V3 position while contacting the other of the first and second electrodes with a left arm of the patient for a time required to measure at least one heart beat (or more if an average beat is to be calculated). The processor is further caused to calculate and display average Leads V4, V5, and V6 from the measured electrocardiogram signals obtained from sequentially placing one of the first and second electrodes in a V4, V5, and V6 position while contacting the other of the first and second electrodes with a right arm of the patient for a time required to measure at least one heartbeat. The resulting 12-lead display and report replicated the 12-lead electrocardiogram produced by a 10-electrode electrocardiograph.

Methods are provided for generating a 12-lead electrocardiogram using an electrocardiograph comprising an electrocardiograph device and a portable computing device. The electrocardiograph device has a first electrode, a second electrode, control circuitry, and a data transmission module, the control circuitry configured to measure electrocardiogram signals between the first and second electrodes. In one embodiment, such a method includes directing, by the portable computing device, a user to place the first electrode and the second electrode at predetermined locations on a patient's body. The portable computing device receives and records location data indicative of the predetermined location on which the first electrode and the second electrode are placed. The control circuitry of the electrocardiograph device receives electrocardiogram signals from the first electrode and the second electrode, and the data transmission module of the electrocardiograph device transmits the electrocardiogram signals to the portable computing device. The portable computing device generates a 12-lead electrocardiogram from the sequentially measured electrocardiogram signals between the first and second electrodes.

BRIEF DESCRIPTION OF THE DRAWINGS

FIG. 7A-FIG. 7E illustrates an example sequential electrode placement used by the electrocardiograph to generate a 12-lead electrocardiogram in accordance with the presently disclosed inventive concepts.

DETAILED DESCRIPTION

Figure 1:
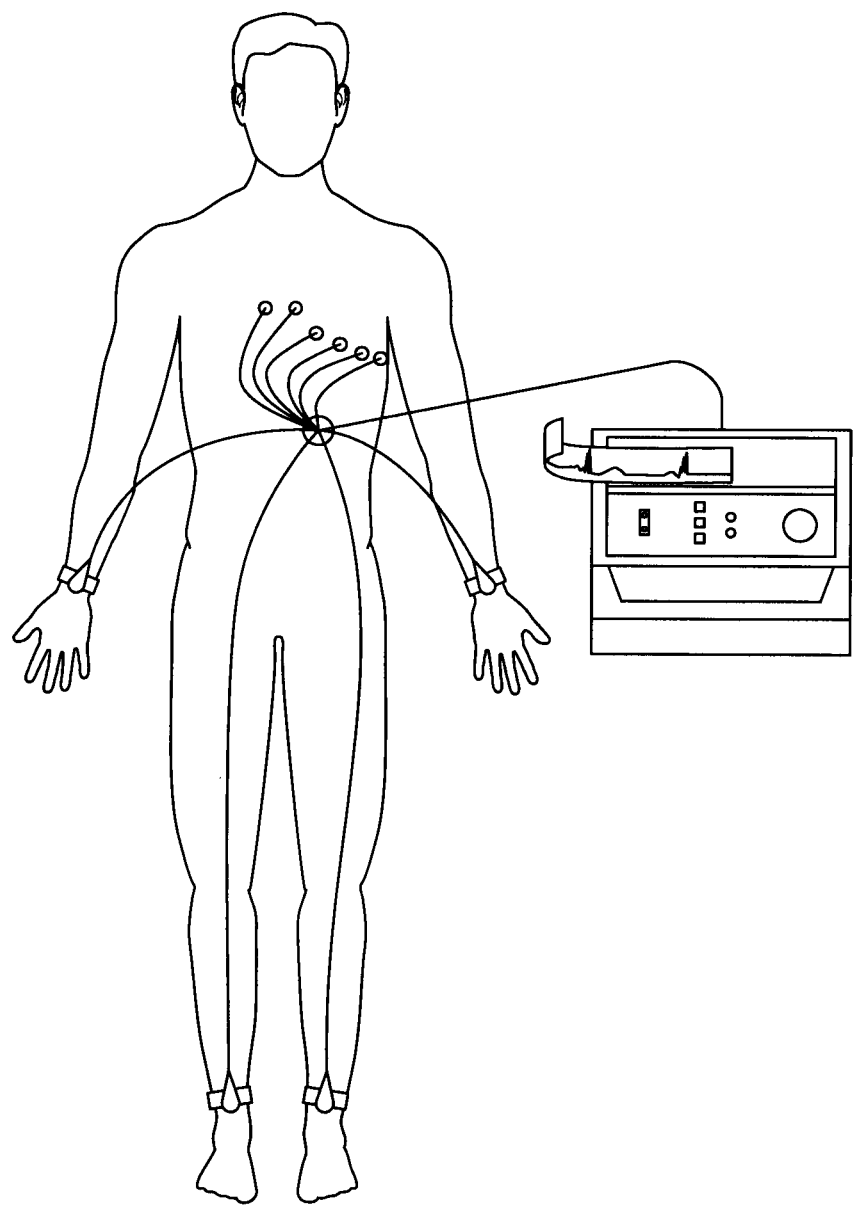
FIG. 1 is a pictorial representation of a prior art electrocardiograph having 10 electrodes positioned on a patient's body for taking a prior art 12-lead electrocardiogram.
Figure 2:
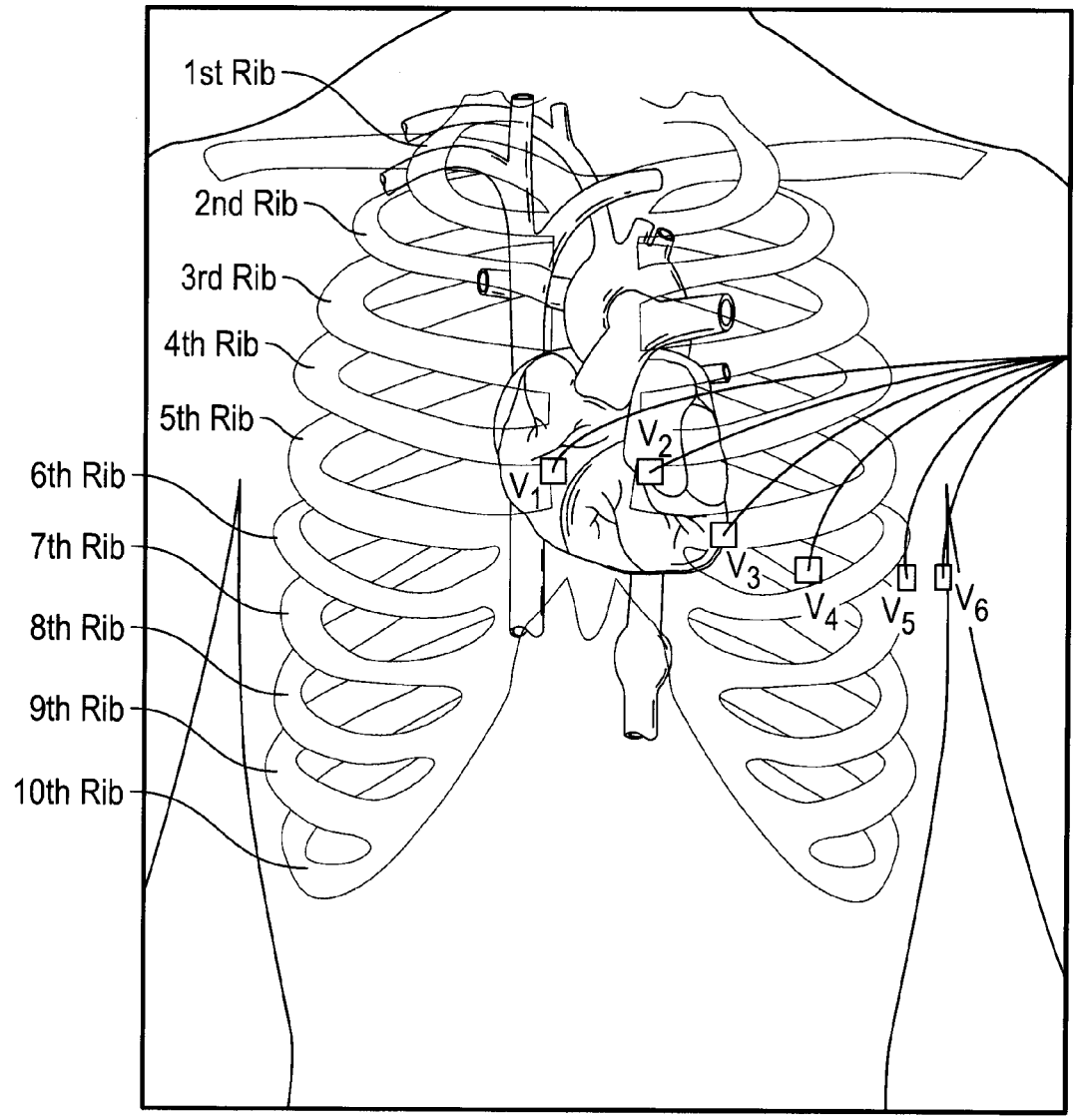
FIG. 2 is a pictorial representation of a chest showing an example of electrode placement on the chest for taking a prior art 12-lead electrocardiogram.
Figure 3:
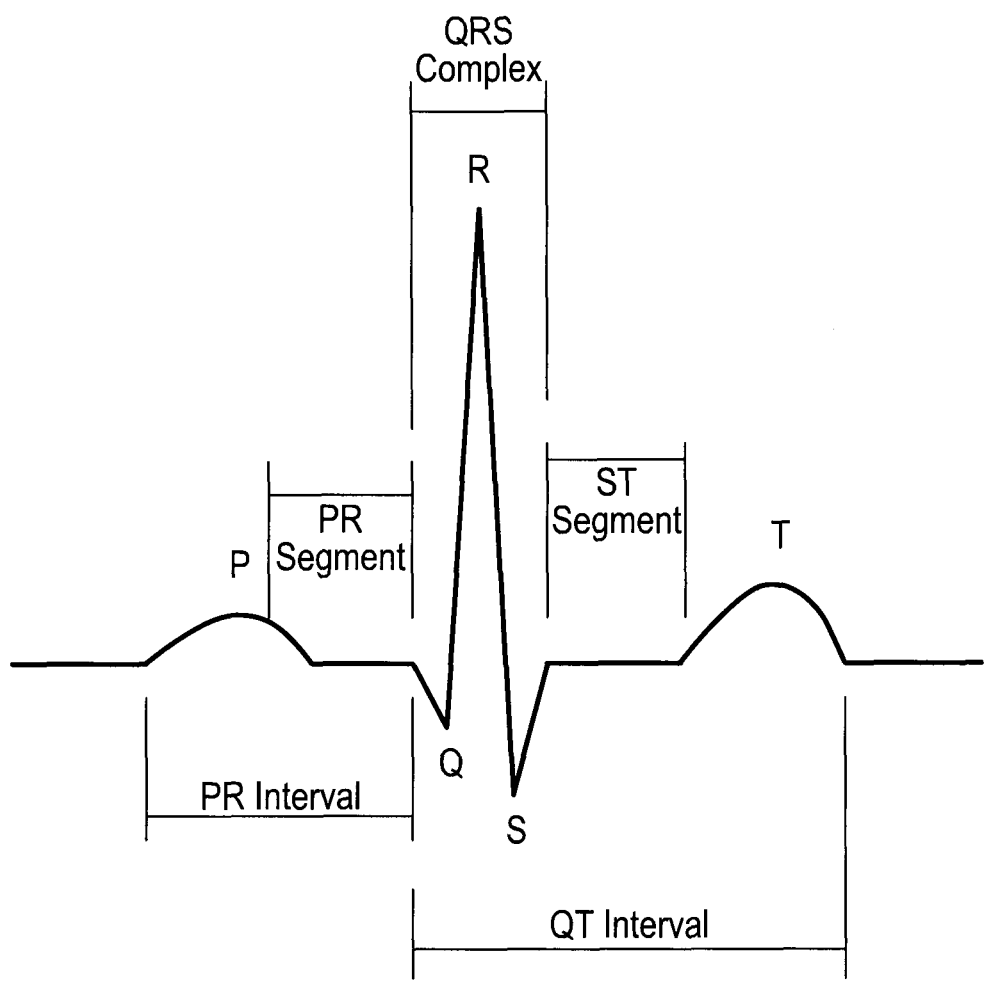
FIG. 3 illustrates an example Lead I annotated to show PQRST waves generated by a 12-lead electrocardiograph.

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 4:
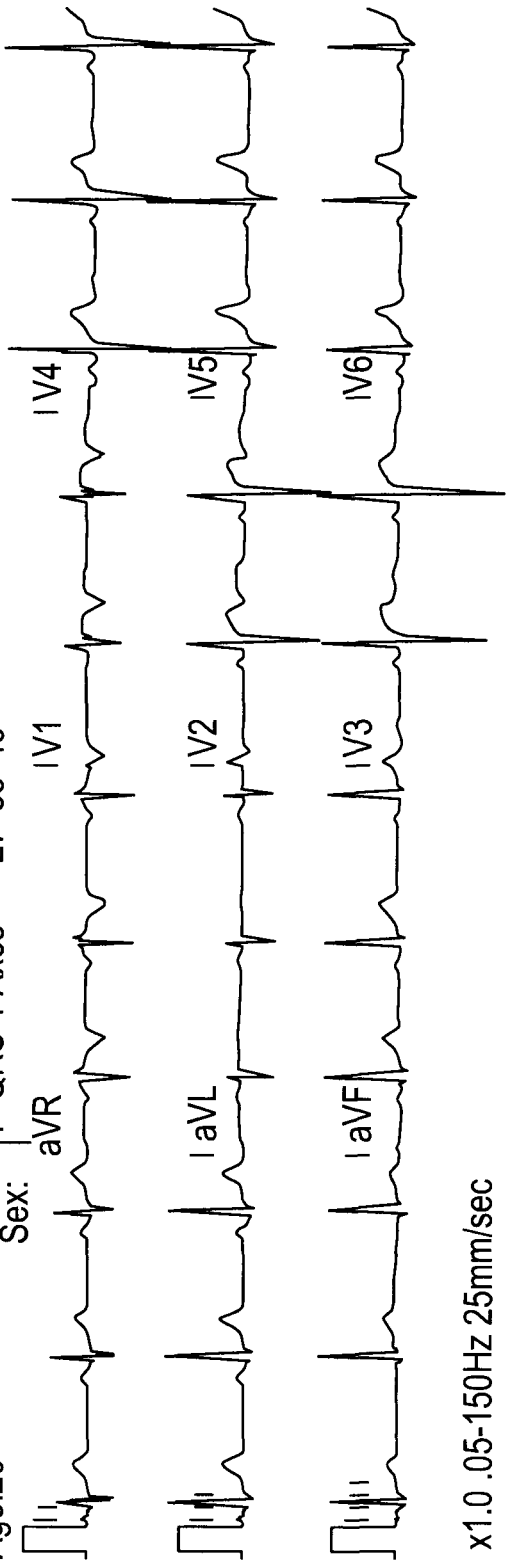
FIG. 4 shows an example 12-lead electrocardiogram in a conventional format.

The term "lead" in electrocardiography causes much confusion because it can be used to refer to two different things. In accordance with common usage, the word "lead" may be used to refer to the electrical cable attaching the electrodes to the electrocardiograph. Alternatively, and as used herein, the word "lead" refers to the tracing of the voltage difference between at least two electrodes. Conventionally, 10 electrodes are used to produce twelve of this type of lead, thereby forming a "12-lead" electrocardiogram as exemplified in FIG. 4.

A "12-lead electrocardiogram format" is used herein and in the appending claims to refer to presentation of electrocardiogram signals from at least Lead I, Lead II, and $V_1$ through $V_6$ leads, and optionally Lead III, aVR, aVL and aVF, displayed over the span of at least one heartbeat using a uniform time scale.

The term "patient" as used herein includes humans and other warm-blooded animals, such as mammals, for example, dogs, cats, horses, and cattle or cold-blooded animals such as reptiles, and refers to the person or animal whose heart-related signals are being measured. The term "user" refers to the one applying the electrodes to the body to measure the ECG. The user can be the same as the patient, or the user can be another such as, for example, a nurse, doctor, or veterinarian.

Figure 5A:
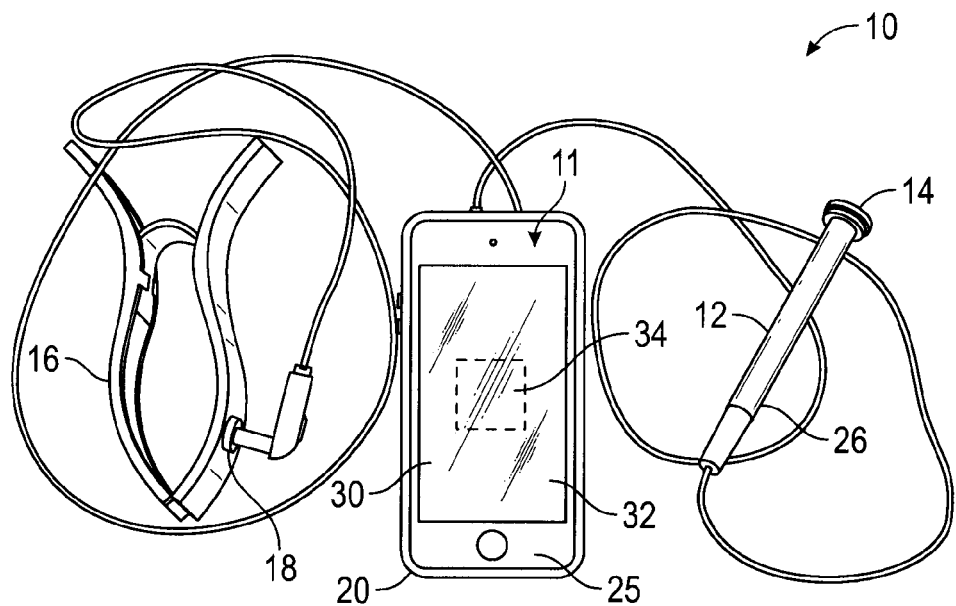
FIG. 5A illustrates a front elevational view of one embodiment of an electrocardiograph constructed in accordance with the presently disclosed and claimed inventive concepts in which the electrocardiograph includes a two-electrode electrocardiograph device and a portable computing device.
Figure 5B:
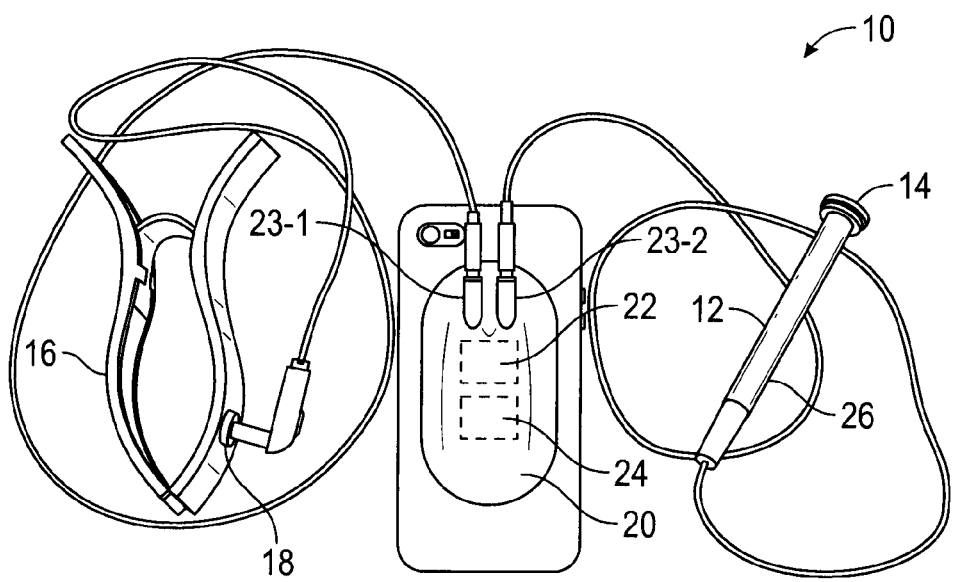
FIG. 5B illustrates a rear elevational view of the electrocardiograph depicted in FIG. 5A.

In general methods, devices, and systems are provided for measuring electrical signals on the body of a patient. Referring now to FIGS. 5A and 5B, shown therein is an exemplary embodiment of an electrocardiograph 8 constructed in accordance with the inventive concepts disclosed and claimed herein. The electrocardiograph 8 includes an electrocardiograph device 10 and a portable computing device 11. The electrocardiograph device 10 as discussed below is a two-electrode device; however, it should be understood that the electrocardiograph device 10 may include more than two electrodes. The electrocardiograph device 10 includes a first electrode assembly 12 having a first electrode 14, a second electrode assembly 16 having a second electrode 18, and a housing 20 containing control circuitry 22 and a data transmission module 24. The first electrode 14 and the second electrode 18 are adapted to measure an electrical signal on a patient's body. The control circuitry 22, can communicate with the first and second electrodes 14 and 18 via ports 23-1 and 23-2, respectively, and is configured to measure electrocardiogram signals between the first and second electrodes 14 and 18, respectively. The electrocardiogram signals can be analog signals indicative of the electrical potentials on a body surface of the patient that are associated with heart muscle activity. The ports 23-1 and 23-2 may be designed to receive analog signals, and may include two, three or four contacts. In some embodiments, the ports 23-1 and 23-2 are standard female connectors in which a three-contact version is known in the art as a TRS connector, where T stands for "tip", R stands for "ring" and S stands for "sleeve". Similarly, two- and four-contact versions are known in the art as TS and TRRS connectors respectively.

The data transmission module 24 is configured to receive the measured electrocardiogram signals and transmit the measured electrocardiogram signals to the portable computing device 11. The data transmission module 24 may transmit the measured electrocardiogram signals to the portable computing device 11 using a wired or wireless transmission system and protocol such as those known in the art as USB, WI-FI®, BLUETOOTH®, NFC, or as audible or ultrasonic sound signals.

While there can be multiple electrodes, in one embodiment there are only two. The first electrode assembly 12 can be configured in any way consistent with its function, i.e., it should include the first electrode 14 in a manner available to make contact with a patient's body on the hands, chest or other parts of the body, to measure an electrical signal for obtaining the patient's electrocardiogram. The first electrode assembly 12 can include a non-conductive hand-held portion 26 as well as the first electrode 14. By using only two electrodes, and sequentially measuring electrocardiogram signals at separate and distinct instants of time as discussed below, a patient can easily measure his or her own electrocardiogram signals and produce a 12-lead electrocardiogram without the need to apply 10 electrodes and adhesives to the body as would be the case using a conventional electrocardiograph.

The second electrode assembly 16 can likewise be configured in any way consistent with its function. In one embodiment, the second electrode assembly 16 is configured to removably attach to an upper limb of the patient. For example, the electrocardiograph device 10 shown in FIGS. 5A and 5B includes a second electrode assembly 16 configured as a spring-hinged cuff. By allowing the second electrode assembly 16 to "grasp" the patient rather than the patient grasping an electrode, little or no electrical "noise" is created by the nerves and adjacent muscles holding the second electrode 18.

Other nonlimiting examples of suitable electrodes include suction cup electrodes, disposable snap electrodes, alligator clip electrode connectors with disposable electrodes, and any combination thereof.

The portable computing device 11 can be implemented as a personal computer, a smart phone, network-capable TV set, TV set-top box, a tablet, an e-book reader, a laptop computer, a desktop computer, a network-capable handheld device, a video game console, a server, and combinations thereof, for example. Preferably, the portable computing device 11 comprises an input device 30, an output device 32, and computer hardware 34 (which is shown in Phantom). The computer hardware 34 may be a system or systems that are able to embody and/or execute the logic of the processes described herein. Logic embodied in the form of software instructions and/or firmware may be executed on any appropriate hardware. For example, logic embodied in the form of software instructions or firmware may be executed on a dedicated system or systems, or on a personal computer system, or on a distributed processing computer system, and/or the like. In some embodiments, logic may be implemented in a stand-alone environment operating on a single computer system and/or logic may be implemented in a networked environment, such as a distributed system using multiple computers and/or processors. The computer hardware 34 of the portable computing device 11 may have a processor and a non-transitory computer readable medium. The term "processor" as used herein may include a single processor or multiple processors working independently and/or together to execute the logic described herein. Exemplary non-transitory computer readable medium may include random access memory, read only memory, flash memory, and combinations thereof. The term non-transitory computer readable medium, as used herein, may be implemented as a single physical device or multiple physical devices of a distributed system that may or may not be logically related.

The input device 30 is capable of receiving information input from a user, and transmitting such information to the computer hardware 34. The input device 30 can be implemented as a keyboard, a touchscreen, a mouse, a trackball, a microphone, a fingerprint reader, an infrared port, a slide-out keyboard, a flip-out keyboard, a cell phone, a PDA, a video game controller, a remote control, a fax machine, and combinations thereof, for example.

The output device 32 outputs information in a form perceivable by a user. For example, the output device 32 can be a computer monitor, a screen, a touchscreen, a speaker, a website, a TV set, a smart phone, a PDA, a cell phone, a fax machine, a printer, a laptop computer, and combinations thereof. It is to be understood that the input device 30 and the output device 32 may be implemented as a single device, such as for example a touchscreen of a smartphone or a tablet.

Figure 5C:
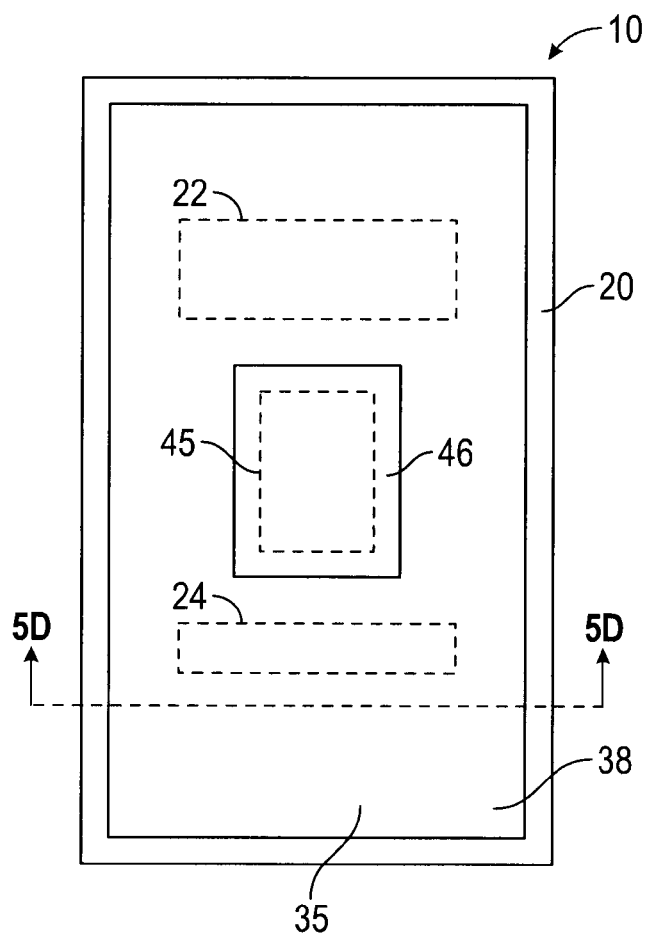
FIG. 5C is a front elevational view of the electrocardiograph device depicted in FIG. 5A in which the electrocardiograph device has been removed from the portable computing device.
Figure 5D:
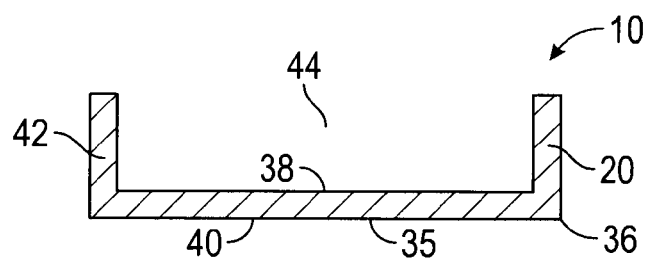
FIG. 5D is a cross-sectional view of the electrocardiograph device depicted in FIG. 5C and taken along the lines 5-5.

In one embodiment, the housing 20 is configured as a protective cover for the portable computing device 11. As shown in FIG. 5C and FIG. 5D, the housing 20 may be provided with a base 35 having a perimeter 36. The base 35 has an interior surface 38 and an opposing exterior surface 40. The housing 20 may also be provided with a rim 42 extending from the interior surface 38 and generally following the perimeter 36 of the base 35. The rim 42 and the interior surface 38 define a space 44 that is sized and adapted to receive the portable computing device 11. The ports 23A and 23B may be proximate to the exterior surface 40 so as to be available when the portable computing device 11 is positioned within the space 44. The base 35, in some embodiments, surrounds and supports the control circuitry 22 and the data transmission module 24. In this embodiment, the base 35 may include a pocket for receiving a power source 45, such as a battery, for powering the control circuitry 22 and the data transmission module 24 and may also include a door 46 proximate to the interior surface 38 for providing access to the pocket such that a user can install and/or replace the power source 45. In other embodiments, the power source 45 maybe a solar cell supported by the base 35 proximate to the exterior surface 40.

The housing 20 may be constructed as a single unit, or multiple units connected together. Exemplary materials forming the housing 20 include plastic, and/or a combination of plastic and elastomers.

Figure 6:
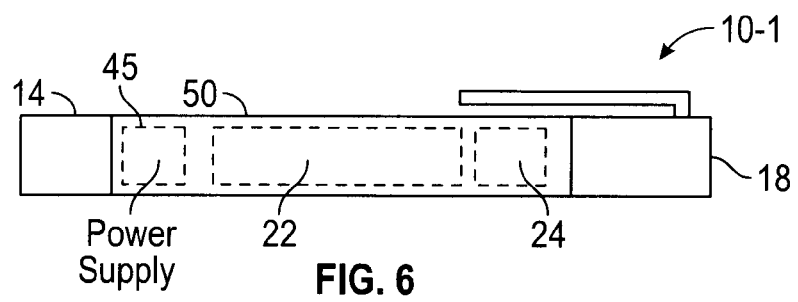
FIG. 6 an other embodiment of a two-electrode electrocardiograph device configured in a pen-shape and constructed in accordance with the inventive concepts disclosed herein.

In another embodiment that is shown in FIG. 6 and labeled by way of example with reference numeral 10-1, the electrocardiograph device combines the first and second electrodes 14 and 18 on opposing ends of a unit 50 shaped like a flash light or pen. For example, the electrocardiograph device 10-1 that is shown in FIG. 6 by way of example has a second electrode 18 on a cylindrical surface of one end of the "pen" touching a holder's hand in use. The first electrode 14 is located on an opposing end and is used to contact the holder's chest, hand or other body part when in use. The electrocardiograph device 10-1 can thus be used to measure the electrical signals between the opposing first and second electrodes 14 and 18, respectively.

The devices and apparatuses disclosed herein can also be configured to use one or more disposable first and second electrodes 14 and 18, respectively, or first and second electrode assemblies 12 and 16, respectively. Use of disposable electrodes or disposable electrode assemblies allows the electrocardiograph device 10 or 10-1 to be used by multiple patients with reduced chance spreading disease by transfer of microbes and bodily fluids from one patient to another.

The first and second electrodes 14 and 18, respectively, can be connected to the control circuitry 22 in a wired or wireless manner. In one embodiment, and as shown in FIGS. 5A and 5B, the first and second electrodes 14 and 18, respectively, are electrically connected to the control circuitry 22 by the ports 23-1 and 23-2, and wires or cables.

The control circuitry 22 measures the small voltage between the first and second electrodes 14 and 18, respectively. In one embodiment, the data transmission module 24 converts the voltage measurements to a frequency modulated electrocardiogram audio signal and transmits the signal to a receiver of the computer hardware 34 of the portable computing device 11 via cable, a wired audio jack connection, wirelessly (using, for example, a BLUETOOTH® connection) or acoustically. The receiver of the portable computing device 11 can thus be a cable connection, audio jack, BLUETOOTH® or similar wireless receiver, or a microphone. In order to provide enhanced privacy, in one embodiment, the data transmission module 24 encrypts the signals prior to transmitting to the portable computing device 11. Numerous encryption techniques are known to those skilled in the art.

Nonlimiting examples of portable computing device 11 having, or adaptable to have, such receivers include smartphones, personal digital assistants (PDAs), tablet personal computers, pocket personal computers, notebook computers, desktop computers, and server computers. The receiver may include an antenna and/or a microphone depending upon the types of signals to be transmitted from the data transmission module 24.

In one embodiment, the electrocardiogram signals are converted to a frequency modulated audio or sound signal having a carrier frequency in a range of from about 1 kHz to about 24 kHz or greater and in this case the receiver of the computer hardware 34 will include a microphone. In another embodiment, the data transmission module 24 converts the electrocardiogram signals to a frequency modulated sound signal having a carrier frequency in a range of from about 18 kHz to about 24 kHz or greater. Nonlimiting examples of suitable ultrasonic transmitters include, but are not limited to, miniature speakers, piezoelectric buzzers, and the like. The ultrasonic signals can be received by, for example, a microphone of the computer hardware 34 of the portable computing device 11.

Figure 7D:
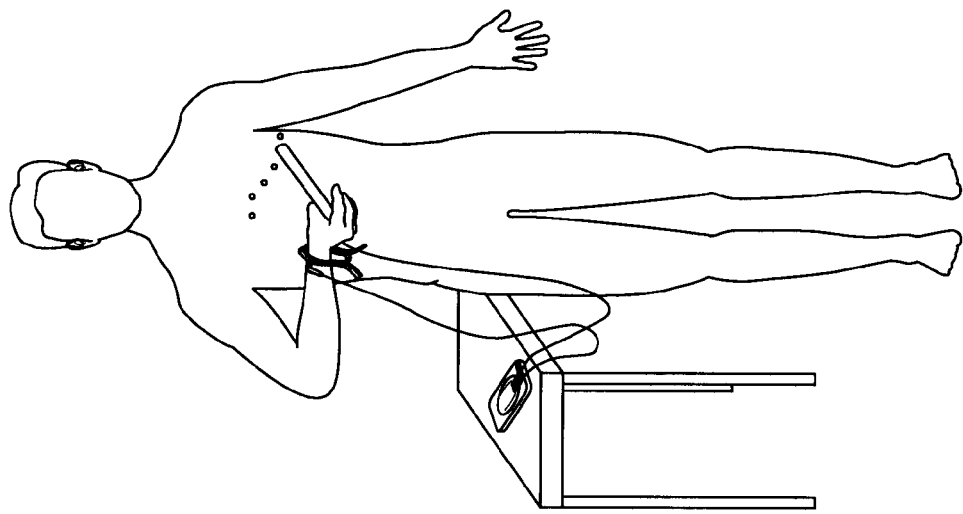
Figure 7E:
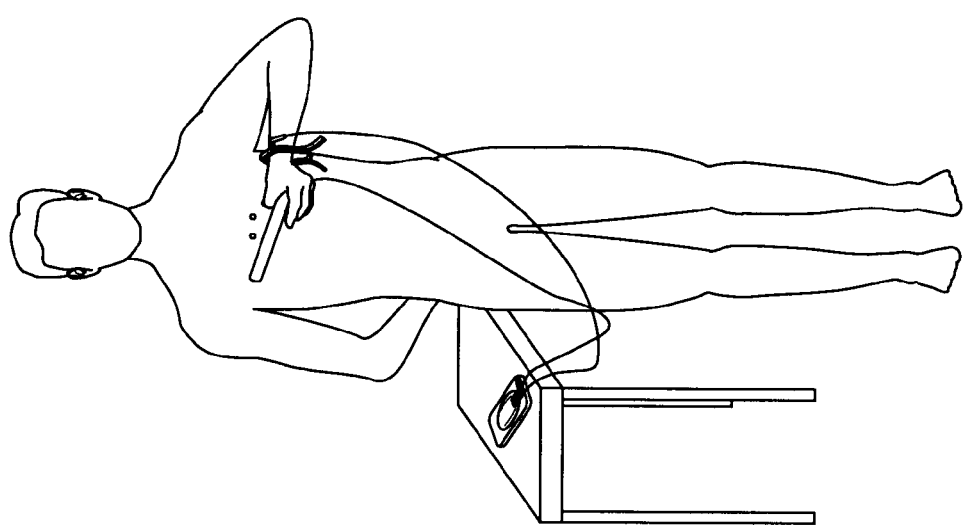

Referring now to FIG. 7, a non-transitory computer readable medium of the computer hardware 34 stores a set of instructions, wherein the set of instructions are capable of being executed by the processor of the portable computing device 11. When the set of instructions are executed, the one or more portable computing device 11 is caused to receive and record electrocardiogram signals between the first electrode 14 and the second electrode 18, while the first and second electrodes 14 and 18, respectively, are sequentially placed in predetermined paired positions on a patient's body at separate and distinct instants of time, and held in each predetermined paired position for multiple heartbeats. The computing device essentially steps the user through the positioning each lead and can, for example, show a picture of a body on a computer screen with the desired electrode positioning indicated by a flashing point. The set of instructions further cause the portable computing device 11 to calculate the electrocardiogram signals into signal sets representing a heartbeat for each paired position, and from the signal sets representing a heartbeat, to calculate average heartbeat representations for each paired position. The set of instructions can then cause the portable computing device 11 to align the average heartbeat representations, and to store and output electrocardiogram data indicative of the average heartbeat representations in a standard 12-lead electrocardiogram format.

For example, ten seconds of each lead can be recorded and an average PQRST computed for each lead from each recording. The limb lead average beats (I, II, and III) can then be time-aligned. Augmented lead average beats are calculated from aligned average limb leads. The V1-V6 beats are averaged and aligned to create a 12-lead report from averaged beats.

The 12-lead electrocardiogram format output can display on the output device 32, such as a display screen of the portable computing device 11 or can be output through a printer. The set of instructions can cause the 12-lead electrocardiogram format output to be retained in a storage memory of the portable computing device 11, or to be transmitted to a computer external to the portable computing device 11, such as a web server via an internet connection on the portable computing device 11.

In one embodiment, the set of instructions can further cause the portable computing device 11 to digitize and demodulate the electrocardiogram signals using technology known to those skilled in the art or technology yet to be developed.

In another embodiment, when the set of instructions are executed, the portable computing device 11 is caused to interact with a user (e.g. via the output device 32) to provide audio and/or textual instructions to direct the placement of the first and second electrodes 14 and 18, respectively, and/or to request the user to confirm placement of the first and second electrodes 14 and 18, respectfully via the input device 30. For example, the portable computing device 11 can be made to provide textual instructions to a user for contacting the first electrode 14 to the patient's left arm and the second electrode 18 to the patient's right arm on a display screen, after which the electrocardiograph device 10 or the electrocardiograph device 10-1 and the portable computing device 11 measures and records the electrical signal between the left arm and right arm for a suitable time interval to correspond to Lead I in a 12-lead ECG. The instructions can further cause the portable computing device 11 to calculate and store an average heartbeat representation for Lead I. A suitable time interval for obtaining heartbeat data for Lead I, and all leads generally, can be between 5 seconds and 30 seconds. Longer times are possible but not necessary.

The set of instructions can further cause the portable computing device 11 to provide instructions to a user, or request placement confirmation from a user, to collect the electrocardiogram data. For example, after the portable computing device 11 has stored the data for Lead I, the portable computing device 11 may provide instructions to the user, or request placement confirmation from the user regarding contacting the first electrode 14 to the patient's left leg and the second electrode 18 to the patient's right arm, wherein the electrical signal measured between the left leg and right arm corresponds to Lead II, and to calculate and store an average heartbeat representation for Lead II.

Similarly, the set of instructions can further cause the portable computing device 11 to provide instructions to a user, or request placement confirmation from a user, regarding contacting the first electrode 14 to the patient's left leg and the second electrode 18 to the patient's left arm, wherein the electrical signal measured between the left leg and the left arm corresponds to Lead III in a 12-lead electrocardiogram and then to analyze the electrical signal corresponding to Lead III to calculate and store an average heartbeat representation for Lead III.

Using the average heartbeat representations Lead I and Lead II, the set of instructions can cause the computing device to calculate aVR, aVL, and aVF. The augmented vector right (aVR) is equal to RA−(LA+LL)/2 or −(I+II)/2. The augmented vector left (aVL) is equal to LA−(RA+LL)/2 or (I−II)/2. The augmented vector foot (aVF) is equal to LL−(RA+LA)/2 or (II−I)/2.

The set of instructions can further cause the portable computing device 11 to provide instructions to a user, or request placement confirmation from the user, for contacting the first electrode 14 with each of the V1, V2, V3, V4, V5, and V6 chest locations while contacting the second electrode 18 to one of the patient's left arm and the patients right arm. The electrical signals measured between each of the V1, V2, V3, V4, V5, and V6 chest locations and the left arm or the right arm correspond to Leads V1, V2, V3, V4, V5, and V6 in a 12-lead electrocardiogram. The set of instructions can then further cause the portable computing device 11 to analyze the electrical signals corresponding to Leads V1, V2, V3, V4, V5, and V6 to calculate average heartbeat representations for Leads V1, V2, V3, V4, V5, and V6.

While not being bound by any particular theory, it has been discovered that use of multiple electrodes to achieve a composite pole such as Wilson's central terminal is not necessary. In one embodiment, the patient's right arm can be used as a negative terminal for each of Leads V1, V2, V3, V4, V5, and V6 captured with conventional placement of electrodes on the chest. In some individuals, however, V1, V2 and V3 measurements do not correlate well. In such individuals, the electrodes must be placed on either side of the heart to achieve duplication of conventional V1, V2 and V3 measurements. It has been definitively demonstrated that in such individuals, the left arm can be used for Leads V1, V2, and V3, while the right arm is used for Leads V4, V5, and V6, and excellent correlation to conventional measurements is achieved.

Once average heartbeat representations are calculated and stored for Leads I, II, III, aVR, aVL, aVF, V1, V2, V3, V4, V5, and V6, the set of instructions can cause the portable computing device 11 to align each of the heartbeat representations based on corresponding characteristics of the heartbeat representations. The averaged and aligned signals can be stored and output in a 12-lead electrocardiogram format.

While it is customary for the voltage measurements to be made in one direction, the software can be made to recognize when the first and second electrodes 14 and 18 are reversed and invert the average heartbeat representation. For example, it is customary for Lead I to measure the left arm (LA) minus the right arm (RA), e.g. I=LA−RA. However, if the first and second electrodes 14 and 18 were reversed such that RA-LA was measured instead, the software would recognize that the first and second electrodes 14 and 18 were reversed and would invert the average heartbeat representation for Lead I to obtain the traditional Lead one output.

Methods for generating a traditional 12-lead electrocardiogram using only two electrodes, e.g. the first and second electrodes 14 and 18, are provided by operating the portable computing device 11 and the above-described electrocardiograph device 10 or 10-1. A 12-lead electrocardiogram can be generated by sequentially measuring electrical signals between the first and second electrodes 14 and 18 at separate and distinct instants of time after the first and second electrodes 14 and 18 are positioned at predetermined locations on a patient's body. Average heartbeat representations for each of the leads can be calculated as described above, and aligned to produce an electrocardiogram having a 12-lead electrocardiogram format.

There are several commonly used 12-lead electrocardiogram formats. The most common format is a 4×3 format; four columns of three leads. The first column includes Limb Leads I, II and III. The second column includes Leads aVR, aVL and aVF. The third column includes Leads V1, V2 and V3, while the fourth column includes Leads V4, V5 and V6.

In some embodiments, the portable computing device 11 is a commercially available smart phone having a standard operating system such as the operating systems identified in the art as "iOS" or "Android." In this embodiment, the electrocardiograph 8 for generating a 12-lead electrocardiogram using only two electrodes can be provided using the above-described electrocardiograph device 10 and software downloadable to the portable computing device 11, wherein the software provides instructions to the portable computing device 11 as described above. In these embodiments, the control circuitry 22 and data transmission module 24 are configured to function and interact with the portable computing device 11 when the portable computing device 11 is executing an application downloadable to the portable computing device 11.

In one embodiment, the systems and methods described above include sending the 12-lead electrocardiogram to a remote server or to a medical professional. In another embodiment, the systems and methods described above include a display and displaying the 12-lead electrocardiogram a on a display screen. Similarly, the systems and methods described above can include a printer and printing the 12-lead electrocardiogram. In yet another embodiment, the methods and systems described above include saving the 12-lead electrocardiogram to a storage memory of the portable computing device 11.

In order to further illustrate the present invention, the following examples are given. However, it is to be understood that the examples are for illustrative purposes only and are not to be construed as limiting the scope of the invention.

Example 1

The above-described system was tested on 121 patients in a clinical trial. Each patient was monitored using the conventional 10 electrodes, i.e., placing 6 electrodes on the patient's chest and one electrode on each of the patient's arms and legs. A conventional 12-lead electrocardiogram report was then prepared for each patient using a traditional stationary electrocardiograph sold under the trademark GE® MAC3500.

The electrocardiograph device 10-1 having the first and second electrodes 14 and 18 in a pen-type configuration was tested on each patient and a conventional format 8-lead report was prepared from the sequential measurements. The 2-electrode electrocardiograph calculated the V1-V6 leads using the right hand (RA) for the negative terminal and then the left hand (LA) for the negative terminal. A statistical analysis was made comparing the 2-electrode electrocardiograph results with the traditional 10-electrode electrocardiograph results.

Figure 8:
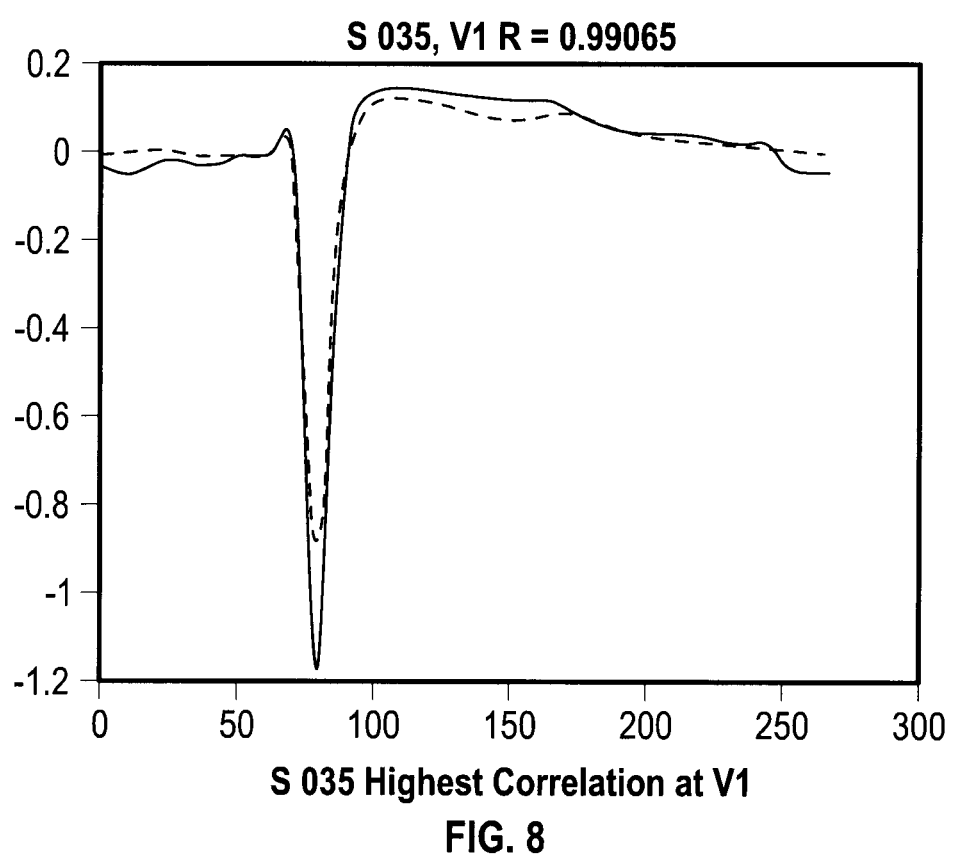
FIG. 8 shows a correlation of V1 leads for Subject 35 of the Example Clinical Trials.

FIG. 8 compares V1 for Subject 35 having the highest correlation between the 10-electrode and the 2-electrode measurements. A correlation coefficient of 0.99 was achieved.

Figure 9:
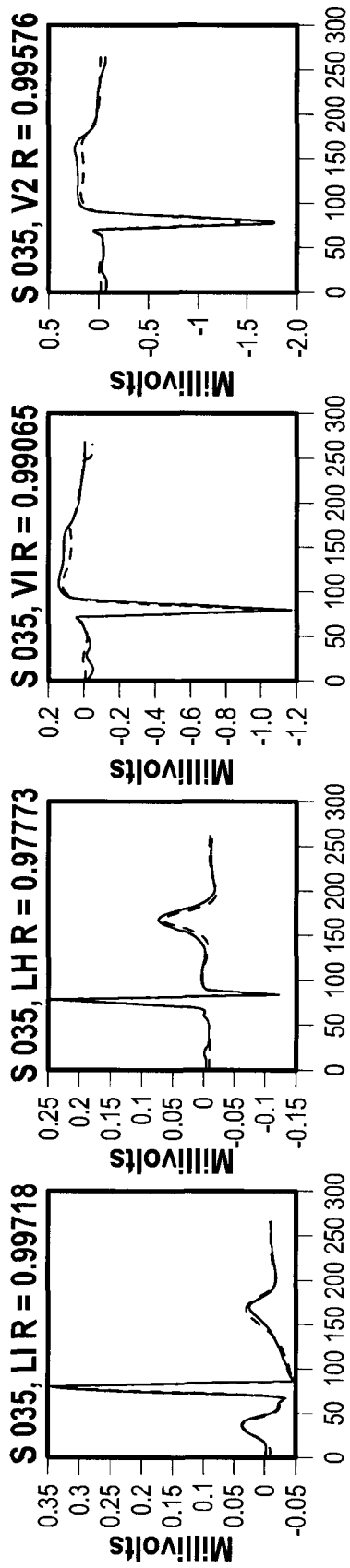
FIG. 9 shows an excellent correlation of leads 1-8 for Subject 35 in the Example Clinical Trials.
Figure 9:
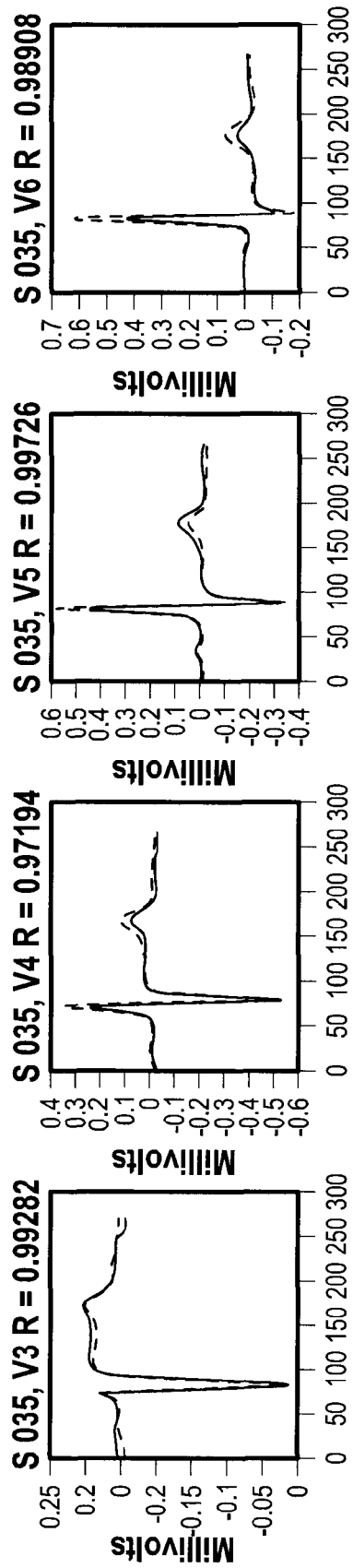

FIG. 9 shows each of the 8 leads for Subject 35, comparing the 10-electrode results with the 2-electrode results. The correlation coefficient averaged over all of the leads was 0.988.

From the above descriptions, it is clear that the presently disclosed and claimed inventive concepts are well-adapted to carry out the objects and to attain the advantages mentioned herein, as well as those inherent in the presently disclosed and claimed inventive concept. While the presented embodiments have been described for purposes of this disclosure, it will be understood that numerous changes may be made which will readily suggest themselves to those skilled in the art and which are accomplished within the spirit of the presently disclosed and claimed inventive concepts.

What is claimed is:

1. An electrocardiograph comprising:
   an electrocardiograph device having (a) a first electrode assembly with a first electrode adapted to measure an electrical signal on a patient's body; (b) a second electrode assembly with a second electrode adapted to measure an electrical signal on the patient's body; (c) control circuitry configured to measure electrocardiogram signals between the first and second electrodes; and (d) a data transmission module configured to transmit the measured electrocardiogram signals to a computing device; and
   a computing device having a non-transitory computer-readable storage medium storing software that includes instructions that when executed by a processor causes the processor to (a) calculate an average PQRST beat from the measured electrocardiogram signals as the first and second electrodes are sequentially placed in Limb Lead I, II, and III positions on a patient's body for a time required to measure at least one heartbeat in each Limb Lead position, the Limb Lead positions known by the processor; (b) use the relationship (Lead III=Lead II−Lead I) to time-align and display Limb Leads I, II, and III; and (c) calculate and display augmented Leads aVR, aVL, and aVF from the time-aligned Limb Leads.

2. The electrocardiograph of claim 1, wherein software further includes instructions that when executed by the processor causes the processor to (d) calculate and display average Leads V1, V2, and V3 from the measured electrocardiogram signals obtained from sequentially placing one of the first and second electrodes in a V1, V2, and V3 position while contacting the other of the first and second electrodes with a left arm of the patient for a time required to measure at least one heart beat; and (e) calculate and display average Leads V4, V5, and V6 from the measured electrocardiogram signals obtained from sequentially placing one of the first and second electrodes in a V4, V5, and V6 position while contacting the other of the first and second electrodes with a right arm of the patient for a time required to measure at least one heartbeat.

3. The electrocardiograph of claim 1 or 2, wherein the data transmission module is configured to transmit the measured electrocardiogram signals to the computing device by wire.

4. The electrocardiograph of claim 1 or 2, wherein the data transmission module is configured to transmit the measured electrocardiogram signals to the computing device wirelessly.

5. The electrocardiograph of claim 1 or 2, wherein at least one of the first and second electrode assemblies comprises a spring-hinged cuff.

6. The electrocardiograph of claim 1 or 2, wherein at least one of the first and second electrode assemblies comprises a disposable electrode.

7. The electrocardiograph device of claim 1 or 2, wherein the portable computing device is a smartphone and the electrocardiograph device further comprises a housing for the control circuitry and the data transmission module, the housing adapted to fit onto or within a protective case for the smartphone.

8. The electrocardiograph device of claim 1 or 2, wherein the data transmission module is further configured to transmit the measured ECG signals as ultrasonic, frequency modulated (FM) sound signals.

9. The electrocardiograph device of claim 1 or 2, wherein the data transmission module is further configured to encrypt and transmit encrypted signals.

10. A non-transitory computer-readable storage medium storing software that includes instructions that when executed by a processor causes the processor to:
    receive and record electrocardiogram signals between a first electrode and a second electrode, the first and second electrodes sequentially placed in predetermined paired positions on a patient's body for a time required to measure at least one heartbeat, the paired positions known by the processor and corresponding to Limb Leads I, II and III, and V1, V2, V3, V4, V5, and V6;
    for each Limb Lead paired position, determine electrocardiogram signal sets representing a heartbeat and calculate average time-aligned heartbeat representations for Limb Leads I, II and III; and
    calculate augmented leads aVR, aVL, and aVF from the average time-aligned heartbeat representations for Limb Leads I, II, and III and output the electrocardiogram signals in a 12-lead electrocardiogram format.

11. The non-transitory computer-readable storage medium of claim 10, wherein the electrocardiogram signals analyzed comprise at least one of wired electrical signals, wireless electromagnetic signals, and acoustic sound signals.

12. The non-transitory computer-readable storage medium of claim 10, wherein the set of instructions, when executed by the processor, further causes the processor to digitize and demodulate frequency modulated electrocardiogram acoustic signals.

13. The non-transitory computer-readable storage medium of claim 10, wherein the set of instructions, when executed by the processor, further causes the processor to interact with a user to identify first and second electrode paired positions corresponding to a lead.

14. The non-transitory computer-readable storage medium of claim 10, wherein the set of instructions, when executed by the processor, further causes the processor to (a) provide instructions to a user or request placement confirmation from the user regarding contacting the first electrode to the patient's left arm and the second electrode to the patient's right arm, wherein the electrical signal measured between the left arm and right arm corresponds to Lead I in a 12-lead electrocardiogram, and (b) analyze the electrical signal corresponding to Lead I to calculate an average heartbeat representation for Lead I.

15. The non-transitory computer-readable storage medium of claim 14, wherein the set of instructions, when executed by the processor, further causes the processor to (c) provide instructions to a user or request placement confirmation from the user regarding contacting the first electrode to the patient's left leg and the second electrode to the patient's right arm, wherein the electrical signal measured between the left leg and right arm corresponds to Lead II in a 12-lead electrocardiogram, and (d) analyze the electrical signal corresponding to Lead II to calculate an average heartbeat representation for Lead II.

16. The non-transitory computer-readable storage medium of claim 15, wherein the set of instructions, when executed by the processor, further causes the processor to (e) provide instructions to a user or request placement confirmation from the user regarding contacting the first electrode to the patient's left leg and the second electrode to the patient's left arm, wherein the electrical signal measured between the left leg and left arm corresponds to Lead III in a 12-lead electrocardiogram, and (f) analyze the electrical signal corresponding to Lead III to calculate an average heartbeat representation for Lead III.

17. The non-transitory computer-readable storage medium of claim 16, wherein the set of instructions, when executed by the processor, further causes the processor to time-align the average heartbeat representations for Lead I and Lead II and calculate aVR, aVL, and aVF average heartbeat representations from the time-aligned average heartbeat representations for Lead I and Lead II.

18. The non-transitory computer-readable storage medium of claim 17, wherein the set of instructions, when executed by the processor, further causes the processor to (g) provide instructions to a user or request placement confirmation from the user regarding contacting the first electrode with each of the V1, V2, V3, V4, V5, and V6 chest locations while contacting the second electrode to one of the patient's left arm and the patients right arm, wherein the electrical signals measured between each of the V1, V2, V3, V4, V5, and V6 chest locations and the left arm or the right arm correspond to Leads V1, V2, V3, V4, V5, and V6 in a 12-lead electrocardiogram, and (h) analyze the electrical signals corresponding to Leads V1, V2, V3, V4, V5, and V6 to calculate average heartbeat representations for Leads V1, V2, V3, V4, V5, and V6.

19. The non-transitory computer-readable storage medium of claim 18, wherein the left arm is used for Leads V1, V2, and V3 and the right arm is used for Leads V4, V5, and V6.

20. The non-transitory computer-readable storage medium of claim 18, wherein the right arm is used for each of Leads V1, V2, V3, V4, V5, and V6.

21. The non-transitory computer-readable storage medium of claim 18, wherein the set of instructions, when executed by the processor, further causes the processor to (i) output the average heartbeat representations for Leads I, II, III, aVR, aVL, aVF, V1, V2, V3, V4, V5, and V6.

22. A method for generating a 12-lead electrocardiogram using an electrocardiograph comprising an electrocardiograph device and a portable computing device, the method comprising:
    operating a portable computing device and an ECG device having a first electrode, a second electrode, control circuitry, and a data transmission module, the control circuitry configured to measure ECG signals between the first and second electrodes, the data transmission module configured to transmit the measured ECG signals to the portable computing device;
    sequentially measuring ECG signals between the first and second electrodes positioned at predetermined locations on a patient's body; and
    using the portable computing device to generate a 12-lead ECG from the sequentially measured ECG signals between the first and second electrodes.

23. The method of claim 22, wherein the step of sequentially measuring ECG signals comprises:
    contacting one of the first and second electrodes with a left arm of a patient while contacting the other of the first and second electrodes with a right arm of the patient to measure an electrical signal corresponding to a Lead I;

contacting one of the first and second electrodes with a left leg of the patient while contacting the other of the first and second electrodes with the right arm of the patient to measure an electrical signal corresponding to a Lead II;

contacting one of the first and second electrodes with the left leg of the patient while contacting the other of the first and second electrodes with the left arm of the patient to measure an electrical signal corresponding to a Lead III;

sequentially contacting one of the first and second electrodes with a V1, V2, V3, V4, V5, and V6 chest location on the patient while contacting the other of the first and second electrodes with the patient's left arm or the patient's right arm to measure electrical signals corresponding to a Leads V1, V2, V3, V4, V5, and V6, respectively.

24. The method of claim 22, wherein the step of sequentially measuring ECG signals comprises:

contacting one the first and second electrodes with a left arm of a patient while contacting the other of the first and second electrodes with a right arm of the patient to measure an electrical signal corresponding to a Lead I;

contacting one of the first and second electrodes with a left leg of the patient while contacting the other of the first and second electrodes with the right arm of the patient to measure an electrical signal corresponding to a Lead II;

contacting one of the first and second electrodes with the left leg of the patient while contacting the other of the first and second electrodes with the left arm of the patient to measure an electrical signal corresponding to a Lead III;

sequentially contacting one of the first and second electrodes with a V1, V2, and V3 chest location on the patient while contacting the other of the first and second electrodes with the left arm of the patient to measure electrical signals corresponding to Leads V1, V2, and V3, respectively; and sequentially contacting one of the first and second electrodes with a V4, V5 and V6 chest location on the patient while contacting the other of the first and second electrodes with the right arm of the patient to measure electrical signals corresponding to Leads V4, V5, and V6, respectively.

25. The method of claim 24, further comprising using the portable computing device to time-align the average heartbeat representations for Lead I and Lead II, and calculate aVR, aVL, and aVF from the time-aligned average heartbeat representations for Lead I and Lead II.

26. The method of claim 25, further comprising using the portable computing device to output the ECG signals in a 12-lead ECG format.

27. A system for generating a 12-lead ECG using two electrodes comprising:

a first electrode assembly having a first electrode adapted to measure an electrical signal on a patient's body;

a second electrode assembly configured to removably attach to an upper limb of the patient, the second electrode assembly having a second electrode adapted to measure an electrical signal on the patient's body;

control circuitry configured to measure ECG signals between the first and second electrodes;

a data transmission module configured to transmit the measured ECG signals to a portable computing device; and a non-transitory computer-readable storage medium storing a set of instructions capable of being executed by one or more computing devices, that when executed by the one or more computing devices causes the one or more computing devices to: (a) analyze ECG signals between a first electrode and a second electrode, the first and second electrodes sequentially placed in predetermined paired positions on a patient's body; (b) average the ECG signals for each paired position to calculate average heartbeat representations for each paired position; and (c) time-align the average heartbeat representations to output in a 12-lead ECG format.

28. The system of claim 27, wherein the first electrode assembly is configured to be hand held.

29. The system of claim 27, wherein the second electrode assembly comprises a spring-hinged cuff.

30. The system of claim 27, wherein the set of instructions, when executed by the one or more computing devices, further causes the one or more computing devices to interact with a user to identify first and second electrode paired positions corresponding to a lead.

31. The system of claim 27, wherein the set of instructions, when executed by the one or more computing devices, further causes the one or more computing devices to (a) provide instructions to a user or request placement confirmation from the user regarding contacting the first electrode to the patient's left arm and the second electrode to the patient's right arm, wherein the electrical signal measured between the left arm and right arm corresponds to Lead I in a 12-lead ECG, and (b) analyze the electrical signal corresponding to Lead I to calculate an average heartbeat representation for Lead I.

32. The system of claim 31, wherein the set of instructions, when executed by the one or more computing devices, further causes the one or more computing devices to (c) provide instructions to a user or request placement confirmation from the user regarding contacting the first electrode to the patient's left leg and the second electrode to the patient's right arm, wherein the electrical signal measured between the left arm and right arm corresponds to Lead II in a 12-lead ECG, and (d) analyze the electrical signal corresponding to Lead II to calculate an average heartbeat representation for Lead II.

33. The system of claim 32, wherein the set of instructions, when executed by the one or more computing devices, further causes the one or more computing devices to (e) provide instructions to a user or request placement confirmation from the user regarding contacting the first electrode to the patient's left leg and the second electrode to the patient's left arm, wherein the electrical signal measured between the left arm and right arm corresponds to Lead III in a 12-lead ECG, and (f) analyze the electrical signal corresponding to Lead III to calculate an average heartbeat representation for Lead III.

34. The system of claim 33, wherein the set of instructions, when executed by the one or more computing devices, further causes the one or more computing devices to time-align the average heartbeat representations for Lead I and Lead II and calculate aVR, aVL, and aVF from the time-aligned average heartbeat representations for Lead I and Lead II.

35. The system of claim 34, wherein the set of instructions, when executed by the one or more computing devices, further causes the one or more computing devices to (g) provide instructions to a user or request placement confirmation from the user regarding contacting the first electrode with each of the V1, V2, V3, V4, V5, and V6 chest locations while contacting the second electrode to one of the patient's left arm and the patients right arm, wherein the electrical signals measured between each of the V1, V2, V3, V4, V5, and V6 chest locations and the left arm or the right arm correspond to Leads V1, V2, V3, V4, V5, and V6 in a 12-lead ECG, and (h) analyze the electrical signals corresponding to Leads V1, V2, V3, V4, V5, and V6 to calculate average heartbeat representations for Leads V1, V2, V3, V4, V5, and V6.

36. The system of claim 35, wherein the left arm is used for Leads V1, V2, and V3 and the right arm is used for Leads V4, V5, and V6.

* * * * *